(12) United States Patent
Hacker et al.

(10) Patent No.: US 7,105,470 B1
(45) Date of Patent: Sep. 12, 2006

(54) HERBICIDAL COMPOSITIONS FOR TOLERANT OR RESISTANT SOYBEAN CROPS

(75) Inventors: Erwin Hacker, Hochheim (DE); Hermann Bieringer, Eppstein (DE); Lothar Willms, Hofheim (DE)

(73) Assignee: Hoechst Schering AgrEvo GmbH, Essen (DE)

(*) Notice: Subject to any disclaimer, the term of this patent is extended or adjusted under 35 U.S.C. 154(b) by 0 days.

(21) Appl. No.: 09/371,612

(22) Filed: Aug. 10, 1999

(30) Foreign Application Priority Data

Aug. 13, 1998  (DE) ................................ 198 36 660

(51) Int. Cl.
*A01N 57/02* (2006.01)
*A01N 43/42* (2006.01)
*A01N 43/52* (2006.01)
*A01P 13/00* (2006.01)

(52) U.S. Cl. ...................... 504/127; 504/128; 504/130; 504/132; 504/139; 504/145

(58) Field of Classification Search ................ 504/127, 504/128
See application file for complete search history.

(56) References Cited

U.S. PATENT DOCUMENTS

| 4,265,654 A | 5/1981 | Takematsu et al. ............. 71/86 |
| 5,198,599 A | 3/1993 | Thill ........................... 800/200 |
| 5,273,894 A | 12/1993 | Strauch et al. ............... 435/129 |
| 5,276,268 A | 1/1994 | Strauch et al. ............... 800/205 |
| 5,599,769 A | 2/1997 | Hacker et al. ................ 504/128 |
| 5,633,434 A | 5/1997 | Schneider et al. ........... 800/205 |
| 5,696,051 A * | 12/1997 | Willms et al. ............... 504/130 |
| 6,165,939 A * | 12/2000 | Agbaje et al. ............... 504/128 |
| 6,586,367 B1 * | 7/2003 | Lee et al. .................... 504/127 |

FOREIGN PATENT DOCUMENTS

| DE | 2856260 | 7/1979 |
| EP | 0 115 673 A2 | 8/1984 |
| EP | 0 242 236 A1 | 10/1987 |
| EP | 0 242 246 A1 | 10/1987 |
| EP | 0 257 542 A2 | 3/1988 |
| EP | 0 275 957 A2 | 7/1988 |
| EP | 0 360 750 A2 | 3/1990 |
| EP | 0 409 815 A1 | 1/1991 |
| WO | WO 91/11517 | 8/1991 |
| WO | WO 92/00377 | 1/1992 |
| WO | WO 92/08353 | 5/1992 |
| WO | WO 96/32013 | 10/1997 |
| WO | WO 97/36488 | 10/1997 |
| WO | WO 98/09525 | 3/1998 |
| WO | WO 98/20144 | 5/1998 |

OTHER PUBLICATIONS

Database Accession No. 1995-89213.
Database Accession No. 1996-90386.
Database Accession No. 1998-89754.
Chemical Abstract, vol. 123, No. 11, No. 135804, 1995.
Chemical Abstract, vol. 128, No. 7, No. 71922, 1997.
Chemical Abstract, vol. 113, No. 7, No. 54241, 1990.
The Pesticide Manual, 10$^{th}$ Edition, pp. 1335-1341, 1995.
Database Accession No. 1996-90678.
Database Accession No. 1998-88956.
Database Accession No. 1998-88957.
Database Accession No. 1996-90692.
Database Accession No. 1997-87701.
Database Accession No. 1995-88943.
Database Accession No. 1997-88300.
Abstract of U.S. Patent No. 5,739,082 issued Apr. 14, 1998.
Katzek et al., Zuckerrube, vol. 47 pp. 217-220, 1998.

* cited by examiner

*Primary Examiner*—S. Mark Clardy
(74) *Attorney, Agent, or Firm*—Frommer Lawrence & Haug LLP

(57) ABSTRACT

Herbicide combinations (A)+(B), if appropriate in the presence of safeners, with an effective content of
(A) broad-spectrum herbicides from the group
 (A1) glufosinate (salts) and related compounds
 (A2) glyphosate (salts) and related compounds such as sulfosate,
 (A3) imidazolinones such as imazethapyr, imazapyr, imazaquin, imazamox or their salts and
 (A4) herbicidal azoles from the group of the protoporphyrinogen oxidase inhibitors (PPO inhibitors) and
(B) one or more herbicides from the group of the compounds consisting of
 (B0) one or more structurally different herbicides from the above-mentioned group (A) and/or
 (B1) foliar- and/or soil-acting herbicides (residual action) which are effective selectively in soybeans against monocotyledonous and predominantly dicotyledonous harmful plants or
 (B2) herbicides which are effective selectively in soybeans against dicotyledonous harmful plants, or
 (B3) foliar- and soil-acting herbicides which are effective selectively in soybeans against monocotyledonous harmful plants or
 (B4) foliar-acting herbicides which are effective selectively in soybeans against monocotyledonous and dicotyledonous harmful plants or
 (B5) nonselective herbicides which can be employed in soybeans for specific purposes, such as paraquat (salts), or
 herbicides from several of groups (B0) to (B5)
are suitable for controlling harmful plants in soybeans which consists of tolerant or resistant mutants or transgenic soybean plants and the soybean crops are tolerant to the herbicides (A) and (B), if appropriate in the presence of safeners, which are contained in the combination.

20 Claims, No Drawings

HERBICIDAL COMPOSITIONS FOR TOLERANT OR RESISTANT SOYBEAN CROPS

The invention is in the field of the crop protection products which can be employed against harmful plants in tolerant or resistant crops of soybeans and which comprise, as herbicidally active substances, a combination of two or more herbicides.

The introduction of tolerant or resistant soybean varieties and soybean lines, in particular transgenic soybean varieties and soybean lines, adds novel active substances which per se are not selective in conventional soybean varieties, to the conventional weed control system. The active substances are, for example, the known broad-spectrum herbicides such as glyphosate, sulfosate, glufosinate, bialaphos and imidazolinone herbicides [herbicides (A)], which can now be employed in the tolerant crops developed specifically for them. The efficacy of these herbicides against harmful plants in the tolerant crops is high, but depends—similarly to other herbicide treatments—on the nature of the herbicide employed, its application rate, the preparation in question, the harmful plants to be controlled, the climatic conditions, the soil conditions etc. Furthermore, the herbicides exhibit weak points (zero effect) against specific species of harmful plants. Another criterion is the duration of action, or the degradation rate of the herbicide. If appropriate, changes in the sensitivity of harmful plants, which may occur upon prolonged use of the herbicides or within a geographical limited area, must also be taken into consideration. The loss of action against individual plants can only be compensated for to some extent by higher application rates of the herbicides, if at all. Moreover, there is always a demand for methods to achieve the herbicidal effect with lower application rates of active substances.

A lower application rate not only reduces the amount of an active substance required for application, but as a rule, also reduces the amount of formulation auxiliaries required. Both reduce the economic outlay and improve the eco-friendliness of the herbicide treatment.

One possibility for improving the use profile of a herbicide may consist in combining the active substance with one or more other active substances which contribute the desired additional properties. However, the combined use of a plurality of active substances does not infrequently lead to phenomena of a physical and biological incompatibility, for example lacking stability of a coformulation, decomposition of an active substance or antagonism of the active substances. In contrast, what is desired are combinations of active substances with a favorable profile of action, high stability and as synergistic an increased action as possible, which allows the application rate to be reduced in comparison with the individual application of the active substances to be combined.

Surprisingly, it has now been found that active substances from the group of the abovementioned broad-spectrum herbicides (A) in combination with other herbicides from group (A) and, if appropriate, specific herbicides (B) interact especially favorably when they are employed in the soybean crops which are suitable for the selective use of the first-mentioned herbicides.

The invention therefore relates to the use of herbicide combinations for controlling harmful plants in soybean crops, wherein the herbicide combination in question has a synergistically active content of (A) a broad-spectrum herbicide from the group of the compounds consisting of
(A1) compounds of the formula (A1),

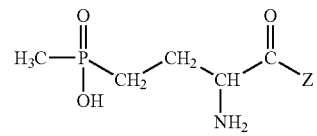

in which Z is a radical of the formula —OH or a peptide radical of the formula —NHCH(CH₃)CONHCH(CH₃)COOH or —NHCH(CH₃)CONHCH[CH₂CH(CH₃)₂]COOH, and their esters and salts, preferably glufosinate and its salts with acids and bases, in particular glufosinate-ammonium, L-glufosinate or its salts, bialaphos and its salts with acids and bases, and other phosphinothricin derivatives, (A2) compounds of the formula (A2) and their esters and salts,

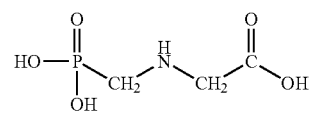

preferably glyphosate and its alkali metal salts or salts with amines, in particular glyphosate-isopropylammonium, and sulfosates, (A3) imidazolinones, preferably imazethapyr, imazapyr, imazamethabenz, imazamethabenz-methyl, imazaquin, imazamox, imazapic (AC 263,222) and their salts and (A4) herbicidal azoles from the protoporphyrinogen-oxidase inhibitors (PPO inhibitors), such as WC9717 (=CGA276854), and (B) one or more herbicides from the group of the compounds which consists of
(B0) one or more structurally different herbicides from the abovementioned group (A) and/or
(B1) foliar- and/or soil-acting herbicides (residual action) which are effective selectively in soybeans against monocotyle-donous and predominantly dicotyledonous harmful plants, and/or
(B2) herbicides which are effective selectively in soybeans against dicotyledonous harmful plants, and/or
(B3) foliar- and soil-acting herbicides which are effective selectively in soybeans against monocotyledonous harmful plants and/or
(B4) foliar-acting herbicides which are effective selectively in soybeans against monocotyledonous and dicotyledonous harmful plants and/or
(B5) nonselective herbicides which can be employed in soybeans for specific purposes, such as paraquat (salts)

and the soybean crops are tolerant to the herbicides (A) and (B) which form a constituent of the combination, if appropriate in the presence of safeners.

In addition to the herbicide combinations according to the invention, other crop protection active substances and adjuvants and formulation auxiliaries conventionally used in crop protection may be used.

The synergistic effects are observed when the active substances (A) and (B) are applied together, but can also be observed upon split application (splitting). Another possibility is to apply the herbicides or herbicide combinations in several portions (sequential application), for example after pre-emergence applications, followed by post-emergence applications or after early post-emergence applications, followed by applications at medium or late post-emergence. Preferred is the simultaneous application of the active substances of the combination in question, if appropriate in several portions. However, a staggered application of the individual active substances of a combination is also possible and may be advantageous in individual cases. Other crop protection agents such as fungicides, insecticides, acaricides and the like, and/or different auxiliaries, adjuvants and/or fertilizer applications may also be integrated into this system application.

The synergistic effects allow the application rates of the individual active substances to be reduced, a more potent action against the same species of harmful plant combined with the same application rate, the control of species to which the action has hitherto not extended (zero effect), an extended application period and/or a reduced number of required individual applications and—as a result for the user—economical and ecologically more advantageous weed control systems.

For example, the combinations of (A)+(B) according to the invention allow synergistically increased effects which far and unexpectedly exceed the effects which can be achieved with the individual active substances (A) and (B).

WO-A-98/09525 has already described a method of controlling weeds in transgenic crops which are resistant to phosphorus-containing herbicides such as glufosinate or glyphosate, herbicide combinations being employed which comprise glufosinate or glyphosate and at least one herbicide from the group consisting of prosulfuron, primisulfuron, dicamba, pyridate, dimethenamid, metolachlor, flumeturon, propaquizafop, atrazine, clodinafop, norflurazone, ametryn, terbuthylazine, simazine, prometryn, NOA-402989 (3-phenyl-4-hydroxy-6-chloropyridazine), a compound of the formula

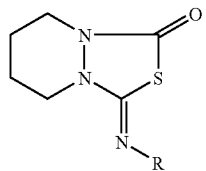

in which R=4-chloro-2-fluoro-5-(methoxycarbonyl methylthio)phenyl (disclosed in U.S. Pat. No. 4,671,819), CGA276854=1-allyloxycarbonyl-1-methylethyl 2-chloro-5-(3-methyl-2,6-dioxo-4-trifluoromethyl-3,6-dihydro-2H-pyrimidin-1-yl)-benzoate (=WC9717, disclosed in U.S. Pat. No. 5,183,492) and 4-oxetanyl 2-{N-[N-(4,6-dimethylpyrimidin-2-yl)aminocarbonyl]aminosulfonyl}benzoate (disclosed in EP-A-496701).

Details on the obtainable effects, or effects which have been obtained, cannot be found in the publication WO-A-98/09525. There are no examples on synergistic effects or on carrying out the method in specific crops, nor are there specific combinations of two, three or more herbicides.

DE-A-2856260 has already disclosed a few herbicide combinations with glufosinate or L-glufosinate and other herbicides such as alloxidim, linuron, MCPA, 2,4-D, dicamba, triclopyr, 2,4,5-T, MCPB and others.

Some herbicide combinations with glufosinate or glyphosate and other herbicides from the sulfonylurea series such as metsulfuron-methyl, nicosulfuron, primisulfuron, rimsulfuron and the like have already been disclosed in WO-A-92/083 53 and EP-A 0 252 237.

However, the use of the combinations for controlling harmful plants has been shown in the publications only with reference to a few plants species or else with reference to no example.

In our experiments, it has been found, surprisingly, that there exist large differences between the usefulness of the herbicide combinations mentioned in WO-A-98/09525 and in the other publications and also of other novel herbicide combinations in crops of plants.

According to the invention, herbicide combinations which can be employed particularly advantageously in tolerant soybean crops are provided.

The compounds of the formulae (A1) to (A5) are known or can be prepared analogously to known processes.

Formula (A1) encompasses all stereoisomers and their mixtures, in particular the racemate and the particular enantiomer which has a biological action, for example L-glufosinate and its salts. Examples of active substances of the formula (A1) are the following:

(A1.1) glufosinate in the narrow sense, i.e. D,L-2-amino-4-[hydroxy(methyl)-phosphinyl]butanoic acid, (A1.2) glufosinate-monoammonium salt, (A1.3) L-glufosinate, L- or (2S)-2-amino-4-[hydroxy(methyl)phosphinyl]butanoic acid (phosphinothricin), (A1.4) L-glufosinate monoammonium salt, (A1.5) bialaphos (or bilanafos), i.e. L-2-amino-4-[hydroxy (methyl)phosphinyl]-butanoyl-L-alanyl-L-alanine, in particular its sodium salt.

The abovementioned herbicides (A1.1) to (A1.5) are absorbed via the green parts of the plants and are known as broad-range herbicides or total herbicides; they are inhibitors of the enzyme glutamine synthetase in plants; see "The Pesticide Manual" 11th Edition, British Crop Protection Council 1997, pp. 643–645 and 120–121. While they can be employed post-emergence for controlling broad-leaved weeds and grass weeds in plantation crops and on non-crop area and, using specific application techniques, also for the in-between-rows treatment of agricultural ground crops such as maize, cotton and the like, the importance of use as selective herbicides in resistant transgenic crops of plants is increasing.

Glufosinate is usually employed in the form of a salt, preferably of the ammonium salt. The racemate of glufosinate, or glufosinate-ammonium, alone is usually applied at rates between 50 and 2000 g of a.s./ha, usually 200 and 2000 g of a.s./ha (=g of a.i./ha=grams of active substance per hectare). At such rates, glufosinate is effective mainly when taken up via the green parts of the plants. However, since it is degraded microbially in the soil within a few days, it has no long-term action in the soil. The same also applies to the related active substance bialaphos sodium (also termed bilanafos-sodium); see "The Pesticide Manual" 11th Ed., British Crop Protection Council 1997 pp. 120–121.

As a rule, markedly less active substance (A1), for example an application rate in the range of 20 to 800, preferably 20 to 600, grams of active substance of glufosinate per hectare (g of a.s./ha or g of a.i./ha) is required in the combinations according to the invention. Similar amounts, preferably amounts which have been converted into moles per hectare, also apply to glufosinate-ammonium and bialafos, or bialafos-sodium.

The combinations with the foliar-acting herbicides (A1) are expediently employed in soybean crops which are resistant or tolerant to the compounds (A1). Some tolerant soybean crops which have been generated by genetic engineering, are already known and are employed in practice; cf. the article in the journal "Zuckerrübe" [Sugarbeet], year 47 (1998), p. 217 et seq.; for the generation of transgenic plants which are resistant to glufosinate, cf. EP-A-0242246, EP-A-242236, EP-A-257542, EP-A-275957, EP-A-0513054).

Examples of compounds (A2) are
(A2.1) glyphosate, i.e. N-(phosphonomethyl)glycine,
(A2.2) glyphosate-monoisopropylammonium salt,
(A2.3) glyphosate-sodium salt,
(A2.4) sulfosate, i.e. N-(phosphonomethyl)glycine-trimesium salt =N-(phosphonomethyl)glycine-trimethylsulfoxonium salt.

Glyphosate is usually employed in the form of a salt, preferably of the monoisopropylammonium salt or the trimethylsulfoxonium salt (=trimesium salt=sulfosate). Based on the free acid glyphosate, the single dose is in the range of 0.020–5 kg of a.s./ha, usually 0.5–5 kg of a.s./ha.

Glyphosate is similar to glufosinate with regard to certain applications, but, in contrast to the latter, it is an inhibitor of the enzyme 5-enolpyruvylshikimate-3-phosphate synthase in plants; see "The Pesticide Manual" 11th Ed., British Crop Protection Council 1997 pp. 646–649. In the combinations according to the invention, application rates in the range of 20 to 1000, preferably 20 to 800 g of a.s. glyphosate are, as a rule, required per ha.

Also, tolerant plants generated by genetic engineering are known for compounds (A2) and have been introduced into practice; cf. "Zuckerrübe" year 47 (1998), p. 217 et seq.; cf. also WO 92/00377, EP-A-115673, EP-A409815.

Examples of imidazolinone herbicides (A3) are
(A3.1) imazapyr and its salts and esters,
(A3.2) imazethapyr and its salts and esters,
(A3.3) imazamethabenz and its salts and esters,
(A3.4) imazamethabenz-methyl,
(A3.5) imazamox and its salts and esters,
(A3.6) imazaquin and its salts and esters, for example the ammonium salt,
(A3.7) imazapic (AC 263,222) and its salts and esters, for example th ammonium salt.

The herbicides inhibit the enzyme acetolactate synthase (ALS) and thus the protein synthesis in plants; they are both soil-acting and foliar-acting and, in some cases, show selectivities in crops; cf. "The Pesticide Manual" 11 th Ed., British Crop Protection Council 1997 pp. 697–699 for (A3.1), pp. 701–703 for (A3.2), pp. 694–696 for (A3.3) and (A3.4), pp. 696–697 for (A3.5), pp. 699–701 for (A3.6) and pp. 5 and 6, reviewed as AC 263,222 (for A3.7). The application rates of the herbicides are usually between 0.01 and 2 kg of a.s./ha, usually 0.1 to 2 kg of a.s./ha; especially (A3.1) from 20–400 g of a.s./ha, preferably 40–360 g of a.s./ha, (A3.2) from 10–200 g of a.s./ha, preferably 20–180 g of a.s./ha, (A3.3) from 100–2000 g of a.s./ha, preferably 150–1800 g of a.s./ha, (A3.4) from 100–2000 g of a.s./ha, preferably 150–1800 g of a.s./ha, (A3.5) from 1–150 g of a.s./ha, preferably 2–120 g of a.s./ha, (A3.6) from 10–900 g of a.s./ha, preferably 20–800 g of a.s./ha, (A3.7) from 5–2000 g of a.s./ha, preferably 10–1000 g of a.s./ha.

In the combinations according to the invention, they are in the range of from 10 to 800 g of a.s./ha, preferably 10 to 200 g of a.s./ha.

The combinations with imidazolinones are expediently employed in soybean crops which are resistant to the imidazolinones. Such tolerant crops are already known. EP-A-0360750, for example, describes the generation of ALS-inhibitor-tolerant plants by selection methods or genetic engineering methods. The herbicide tolerance of the plants is generated by means of an elevated ALS content in the plants. U.S. Pat. No. 5,198,599 describes sulfonylurea- and imidazolinone-tolerant plants which have been obtained by selection methods.

Examples of PPO inhibitors (A4) are:
(A4.1) pyraflufen and its esters, such as pyraflufen-ethyl,
(A4.2) carfentrazone and its esters, such as carfentrazone-ethyl,
(A4.3) oxadiargyl
(A4.4) sulfentrazone
(A4.5) WC9717 or CGA276854=1-allyloxycarbonyl-1-methylethyl 2-chloro-5-(3-methyl-2,6-dioxo-4-trifluoromethyl-3,6-dihydro-2H-pyrimidin-1-yl)-benzoate (disclosed in U.S. Pat. No. 5,183,492).

The abovementioned azoles are known as inhibitors of the enzyme protoporphyrinogen oxidase (PPO) in plants; see "The Pesticide Manual" 11th Ed., British Crop Protection Council 1997 pp. 1048–1049 for (A4.1), pp. 191–193 for (A4.2), pp. 904–905 for (A4.3) and pp. 1126–1127 for (A4.4). Tolerant crops of plants have already been described. As a rule, the application rates of the azoles are in the range of 1 to 1000 g of a.s./ha, preferably 2 to 800 g of a.s./ha, in particular the following application rates of the individual active substances:

(A4.1) 1 to 100, preferably 2 to 80 g of a.s./ha, (A4.2) 1 to 500 g of a.s./ha, preferably 5–400 g of a.s./ha, (A4.3) 10 to 1000 g of a.s./ha, preferably 20–800 g of a.s./ha, (A4.4) 10 to 1000 g of a.s./ha, preferably 20–800 g of a.s./ha, (A4.5) 10 to 1000 g of a.s./ha, preferably 20–800 g of a.s./ha.

Some plants which are tolerant to PPO inhibitors are already known.

Examples of suitable components (B) are compounds of subgroups (B0) to (B4) (indicated in the following by the preferred application rates indicated in brackets), i.e. one or more herbicides from the group which consists of (B0) one or more structurally different herbicides from the abovementioned group (A) and/or (B1) foliar-acting and/or soil-acting (residual action) herbicides which are effective selectively in soybeans against monocotyledonous and predominantly dicotyledonous harmful plants, such as (B1.1) trifluralin (PM, pp. 1248–1250) (250 to 5000 g of a.s./ha, in particular 400 to 4000 g of a.s./ha), (B1.2) m tribuzin (PM, pp. 840–841) (250 to 4000 g of a.s./ha, in particular 500 to 3000 g of a.s./ha), (B1.3) clomazone (PM, pp. 256–257) (150 to 50009 of a.s./ha, in particular 200 to 3000 g of a.s./ha), (B1.4) pendimethalin (PM, pp. 937–939) (250 to 4000 g of a.s./ha, in particular 500 to 3000 g of a.s./ha), (B1.5) metolachlor (PM, pp. 833–834) also in the optically active form S-metolachlor (100 to 5000 g of a.s./ha, in particular 200 to 4000 g of a.s./ha),
(B1.6) flumetsulam (PM, pp. 573–574) (5 to 300 g of a.s./ha, in particular 10 to 100 g of a.s./ha),
(B1.7) dimethenamid (PM, pp. 409410) (20 to 5000 g of a.s./ha, in particular 50 to 4000 g of a.s./ha),
(B1.8) alachlor (PM, pp. 23–24) (250 to 5000 g of a.s./ha, in particular 500 to 4000 g of a.s./ha),
(B1.9) linuron (PM, pp. 751–753) (250 to 5000 g of a.s./ha, in particular 500 to 4000 g of a.s./ha),
(B1.10) sulfentrazone (PM, pp. 1126–1127) (50 to 2000 g of a.s./ha, in particular 70 to 1500 g of a.s./ha),
(B1.11) ethalfluralin (PM, pp. 473–474) (250 to 5000 g of a.s./ha, in particular 500 to 4000 g of a.s./ha),
(B1.12) fluthiamide (BAY FOE 5043, flufenacet) (PM, pp. 82–83) (50 to 5000 g of a.s./ha, in particular 70 to 4000 g of a.s./ha),
(B1.13) norflurazon (PM, pp. 886–888), (500 to 5000 g of a.s./ha, in particular 750 to 4000 g of a.s./ha) and/or
(B1.14) vernolate (PM, pp. 1264–1266), (250 to 5000 g of a.s./ha, in particular 500 to 4000 g of a.s./ha) and/or, if appropriate,
(B1.15) flumioxazin (PM, pp. 576–577), (10 to 500 g of a.s./ha, in particular 20 to 400 g of a.s./ha) and/or
(B2) herbicides which are effective selectively in soybeans against dicotyledonous harmful plants, for example
(B2.1) chlortoluron, chlorotoluron (PM, pp. 229–231) (250 to 5000 g of a.s./ha, in particular 500 to 4000 g of a.s./ha),
(B2.2) bentazone (PM, pp. 109–111) (250 to 5000 g of a.s./ha, in particular 500 to 4000 g of a.s./ha),
(B2.3) thifensulfuron and its esters, in particular the methyl ester (PM, pp. 1188–1190) (1 to 120 g of a.s./ha, in particular 2 to 90 g of a.s./ha),
(B2.4) oxyfluorfen (PM, pp. 919–921) (40 to 800 g of a.s./ha, in particular 60 to 600 g of a.s./ha),
(B2.5) lactofen (PM, pp. 747–748) (20 to 400 g of a.s./ha, in particular 30 to 300 g of a.s./ha),
(B2.6) fomesafen (PM, pp. 616–618) (250 to 5000 g of a.s./ha, in particular 500 to 4000 g of a.s./ha),
(B2.7) flumiclorac (PM, pp. 575–576) and its esters such as the pentyl ester (10 to 400 g of a.s./ha, in particular 20 to 300 g of a.s./ha),
(B2.8) acifluorfen and its sodium salt (PM, pp. 12–14) (40 to 800 g of a.s./ha, in particular 60 to 600 g of a.s./ha),
(B2.9) 2,4-DB (PM, pp. 337–339) and its esters and salts (250 to 5000 g of a.s./ha, in particular 500 to 4000 g of a.s./ha) and/or
(B2.10) 2,4-D (PM, pp. 323–327) and its esters and salts (250 to 5000 g of a.s./ha, in particular 500 to 4000 g of a.s./ha) and/or, if appropriate,
(B2.11) chlorimuron and salts and esters such as chlorimuron-ethyl (PM, pp. 217–218) (200 to 4000 g of a.s./ha, in particular 500 to 3000 g of a.s./ha),
(B2.12) cloransulam and its salts and esters such as cloransulam-methyl (PM, p. 265) (1 to 150 g of a.s./ha, in particular 3 to 120 g of a.s./ha),
(B2.13) diclosulam (cf. AG CHEM New Compound Review, Vol. 17, (1999) page 37, triazolopyrimidin-sulfonamide herbicide), (5 to 150 g of a.s./ha, in particular 10–20 g of a.s./ha),
(B2.14) fluthiacet and its salts and esters such as fluthiacet-methyl (K1H-9201; PM, pp. 606–608) (1–50 g of a.s./ha, in particular 2–40 g of a.s./ha) and/or
(B2.15) oxasulfuron (PM, pp. 911–912) (10–300 g of a.s./ha, in particular 20–200 g of a.s./ha) and/or (B3) foliar- and soil-acting herbicides which are effective selectively in soybeans against monocotyledonous harmful plants, for example cyclohexanediones from the group consisting of
(B3.1) sethoxydim (PM, pp. 1101–1103) (50 to 3000 g of a.s./ha, in particular 100 to 2000 g of a.s./ha),
(B3.2) cycloxydim (PM, pp. 290–291) (10 to 1000 g of a.s./ha, in particular 30 to 800 g of a.s./ha) and
(B3.3) clethodim (PM, pp. 250–251) (10 to 800 g of a.s./ha, in particular 20 to 600 g of a.s./ha) and/or
(B4) foliar-acting herbicides which are effective selectively in soybeans against monocotyledonous harmful plants, for example (het)aryloxyphenoxy herbicides such as
(B4.1) quizalofop-P and its esters such as the ethyl or terfuryl ester (PM, pp. 1089–1092), also in the form of the mixtures with the other optical isomer, i.e. racemic quizalofop and its esters (10–300 g of a.s./ha, in particular 20–250 g of a.s./ha),
(B4.2) fenoxaprop-P and its esters such as the ethyl ester (PM, pp. 519–520) (10 to 300 g of a.s./ha, in particular 20 to 250 g of a.s./ha), also in the form of the mixtures with the other optical isomer, i.e. as racemic fenoxaprop-ethyl,
(B4.3) fluazifop-P and its esters such as the butyl ester (PM, pp. 556–557) (20 to 1500 g of a.s./ha, in particular 30 to 1200 g of a.s./ha), also in the form of the mixtures with the other optical isomer, i.e. as racemic fluazifop-butyl,
(B4.4) haloxyfop and haloxyfop-P and its esters such as the methyl or the etotyl ester (PM, pp. 660–663) (10–300 g of a.s./ha, in particular 20 to 250 g of a.s./ha) and/or
(B4.5) propaquizafop (PM, pp. 1021–1022) (10–300 g of a.s./ha, in particular 20–250 g of a.s./ha) and/or
(B5) nonselective herbicides which can be employed in soybeans for specific purposes, e.g.
(B5.1) paraquat (salts) such as paraquat dichloride (PM, pp. 923–925) (250 to 5000 g of a.s./ha, in particular 500 to 4000 g of a.s./ha).

In the case of active substances based on carboxylic acids or other active substances which form salts or esters, the specification of the herbicides by the common name of the acid is generally also intended to encompass the salts and esters, preferably the commercially available salts and esters, in particular the current commercial form of the active substance.

The application rates of the herbicides (B) may vary greatly from herbicide to herbicide (cf. the information on the group consisting of the compounds (A) and (B)). The following ranges are rules of thumb:

Compounds (B0): 5–2000 g a.s./ha,

Compounds (B1): 5–5000 g a.s./ha, preferably 10–5000 g a.s./ha,

Compounds (B2): 1–5000 g a.s./ha, preferably 1–3000 g a.s./ha,

Compounds (B3): 10–3000 g a.s./ha, preferably 10–1000 g a.s./ha,

Compounds (B4): 10–1500 g a.s./ha, preferably 5–500 g a.s./ha, Compounds (B5): 250–5000 g a.s./ha, preferably 100–2000 g a.s./ha.

The ratios of compounds (A) and (B) can be deduced from the abovementioned application rates for the individual substances, for example the following ratios are of particular interest:

(A):(B) in the range from 2000:1 to 1:2000, preferably 2000:1 to 1:1000, in particular 200:1 to 1:100, (A):(B0) from 2000:1 to 1:2000, preferably 400:1 to 1:400, in particular 200:1 to 1:200, (A1):(B1) from 400:1 to 1:500, preferably from 200:1 to 1:250, in particular from 200:1 to 1:200, very particularly 200:1 to 1:100, (A1):(B2) from 1500:1 to 1:200, preferably 500:1 to 1:200, in particular 200:1 to 1:100, (A1):(B3) from 150:1 to 1:150, preferably 150:1 to 1:100, in particular 80:1 to 1:10, (A1):(B4) from 300:1 to 1:100, preferably 300:1 to 1:30, in particular 100:1 to 1:10, (A2):(B1) from 200:1 to 1:250, preferably 200:1 to 1:200, in particular from 200:1 to 1:50, (A2):(B2) from 2000:1 to 1:250, preferably from 500:1 to 1:200, in particular from 300:1 to 1:200, (A2):(B3) from 200:1 to 1:150, preferably from 200:1 to 1:100, (A2):(B4) from 300:1 to 1:100, preferably from 100:1 to 1:60, in particular from 100:1 to 1:10, (A3):(B1) from 300:1 to 1:2500, preferably from 200:1 to 1:2000, in particular 300:1 to 1:1000, very particularly from 100:1 to 1:200, (A3):(B2) from 3000:1 to 1:3000, preferably from 500:1 to 1:2000, in particular from 500:1 to 1:500, (A3):(B3) preferably from 300:1 to 1:1000, in particular from 100:1 to 1:200, (A3):(B4) from 200:1 to 1:800, preferably from 80:1 to 1:600, in particular 40:1 to 1:100, (A4):(B1) from 300:1 to 1:2500, preferably from 150:1 to 1:2000, in particular 20:1 to 1:1000, very particularly from 10:1 to 1:300, (A4):(B2) from 1500:1 to 1:2500, preferably from 750:1 to 1:2000, in particular 200:1 to 1:500, very particularly from 50:1 to 1:100, (A4):(B3) from 150:1 to 1:750, preferably from 75:1 to 1:1000, in particular 20:1 to 1:200, very particularly from 10:1 to 1:100, (A4):(B4) from 150:1 to 1:750, preferably from 75:1 to 1:600, in particular from 40:1 to 1:1.00, very particularly.

In the case of the combination of a compound (A) with one or more compounds (B0), this is, according to the definition, a combination of two or more compounds from group (A). Because of the broad-spectrum herbicides (A), the condition for such a combination is that the transgenic plants or mutants show cross-resistance to various herbicides (A). Such cross-resistances in transgenic plants have already been disclosed; cf. WO-A-98/20144.

In individual cases, it may be meaningful to combine one or more of the compounds (A) with more than one compound (B), preferably from amongst classes (B1), (B2), (B3), (B4) and (B5).

Moreover, the combinations according to the invention can be employed together with other active substances, for example from the group of the safeners, fungicides, insecticides and plant growth regulators, or from the group of the additives and formulation auxiliaries conventionally used in crop protection. Additives are, for example, fertilizers and colors.

Preferred are herbicide combinations of one or more compounds (A) with one or more compounds from the group (B1) or (B2) or (B3) or (B4) or (B5).

Also preferred are combinations of one or more compounds (A), for example (A1.2)+(A2.2), preferably of a compound (A), with one or more compounds (B) as shown in the scheme:

(A)+(B1)+(B2), (A)+(B1)+(B3), (A)+(B1)+(B4), (A)+(B2)+(B3), (A)+(B2)+(B4), (A)+(B3)+(B4), (A)+(B1)+(B2)+(B3), (A)+(B1)+(B2)+(B4), (A)+(B1)+(B3)+(B4), (A)+(B2)+(B3)+(B4).

Combinations to which one or more other active substances of a different structure [active substances (C)] are added are also according to the invention, for example (A)+(B1)+(C), (A)+(B2)+(C), (A)+(B3)+(C) or (A)+(B4)+(C) (A)+(B1)+(B2)+(C), (A)+(B1)+(B3)+(C), (A)+(B1)+(B4)+(C), (A)+(B2)+(B4)+(C) or (A)+(B3)+(B4)+(C).

The preferred conditions illustrated hereinbelow also apply to combinations of the last-mentioned type with three or more active substances, in particular to two-way-combinations according to the invention, mainly when they contain the two-way-combinations according to the invention and with respect to the relevant two-way-combinations.

The use of the following combinations is of particular interest:

(A1.1)+(B1.1), (A1.1)+(B1.2), (A1.1)+(B1.3), (A1.1)+(B1.4), (A1.1)+(B1.5), (A1.1)+(B1.6), (A1.1)+(B1.7), (A1.1)+(B1.8), (A1.1)+(B1.9), (A1.1)+(B1.10), (A1.1)+(B1.11), (A1.1)+(B1.12), (A1.1)+(B1.13), (A1.1)+(B1.14), (A1.1)+(B1.15), (A1.1)+(B2.1), (A1.1)+(B2.2), (A1.1)+(B2.3), (A1.1)+(B2.4), (A1.1)+(B2.5), (A1.1)+(B2.6), (A1.1)+(B2.7), (A1.1)+(B2.8), (A1.1)+(B2.9), (A1.1)+(B2.10), (A1.1)+(B2.11), (A1.1)+(B2.12), (A1.1)+(B2.13), (A1.1)+(B2.14), (A1.1)+(B2.15), (A1.1)+(B3.1), (A1.1)+(B3.2), (A1.1)+(B3.3), (A1.1)+(B4.1), (A1.1)+(B4.2), (A1.1)+(B4.3), (A1.1)+(B4.4), (A1.1)+(B4.5), (A1.1)+(B5.1); (A1.2)+(B1.1), (A1.2)+(B1.2), (A1.2)+(B1.3), (A1.2)+(B1.4), (A1.2)+(B1.5), (A1.2)+(B1.6), (A1.2)+(B1.7), (A1.2)+(B1.8), (A1.2)+(B1.9), (A1.2)+(B1.10), (A1.2)+(B1.11), (A1.2)+(B1.12), (A1.2)+(B1.13), (A1.2)+(B1.14), (A1.2)+(B1.15), (A1.2)+(B2.1), (A1.2)+(B2.2), (A1.2)+(B2.3), (A1.2)+(B2.4), (A1.2)+(B2.5), (A1.2)+(B2.6), (A1.2)+(B2.7), (A1.2)+(B2.8), (A1.2)+(B2.9), (A1.2)+(B2.10), (A1.2)+(B2.11), (A1.2)+(B2.12), (A1.2)+(B2.13), (A1.2)+(B2.14), (A1.2)+(B2.15), (A1.2)+(B3.1), (A1.2)+(B3.2), (A1.2)+(B3.3), (A1.2)+(B4.1), (A1.2)+(B4.2), (A1.2)+(B4.3), (A1.2)+(B4.4), (A1.2)+(B4.5), (A1.2)+(B5.1); (A2.2)+(B1.1), (A2.2)+(B1.2), (A2.2)+(B1.3), (A2.2)+(B1.4), (A2.2)+(B1.5), (A2.2)+(B1.6), (A2.2)+(B1.7), (A2.2)+(B1.8), (A2.2)+(B1.9), (A2.2)+(B1.10), (A2.2)+(B1.11), (A2.2)+(B1.12), (A2.2)+(B1.13), (A2.2)+(B1.14), (A2.2)+(B1.15), (A2.2)+(B2.1), (A2.2)+(B2.2), (A2.2)+(B2.3), (A2.2)+(B2.4), (A2.2)+(B2.5), (A2.2)+(B2.6), (A2.2)+(B2.7), (A2.2)+(B2.8), (A2.2)+(B2.9), (A2.2)+(B2.10), (A2.2)+(B2.11), (A2.2)+(B2.12), (A2.2)+(B2.13), (A2.2)+(B2.14), (A2.2)+(B2.15), (A2.2)+(B3.1), (A2.2)+(B3.2), (A2.2)+(B3.3), (A2.2)+(B4.1), (A2.2)+(B4.2), (A2.2)+(B4.3), (A2.2)+(B4.4), (A2.2)+(B4.5), (A2.2)+(B5.1).

Also of particular interest is the use according to the invention of the combinations with one or more herbicides from the group (A), preferably (A1.2) or (A2.2), in particular (A1.2), and with one or more herbicides, preferably one herbicide, from the group consisting of (B0') one or more structurally different herbicides from the abovementioned group (A) and/or (B1') foliar-acting and/or soil-acting (residual action) herbicides which are effective selectively in soybeans against monocotyledonous and predominantly dicotyledonous harmful plants, such as trifluralin, metribuzin, clomazone, pendimethalin, flumetsulam, alachlor, sulfentrazone, ethalfluralin, fluthiamide and/or vernolate and/or, if appropriate, flumioxazin and/or (B2') herbicides which are effective selectively in soybeans against dicotyledonous harmful plants, for example chlortoluron, bentazone, oxyfluorfen, lactofen, fomesafen, flumiclorac and/or acifluorfen and/or, if appropriate, cloransulam, diclosulam, fluthiacet and/or oxasulfuron and/or (B3') foliar- and soil-acting herbicides which are effective selectively in soybeans against monocotyledonous harmful plants, for example sethoxydim, cycloxydim and/or clethodim and/or (B4') foliar-acting herbicides which are effective selectively in soybeans against monocotyledonous harmful plants, for example (het)aryloxyphenoxy herbicides such as quizalofop-P, quizalofop, fenoxaprop-P, fenoxaprop, fluazifop-P, fluazifop, haloxyfop and/or haloxyfop-P and/or (B5') nonselective herbicides which can be employed in soybeans for specific purposes, such as paraquat (salts) or of herbicides from several of the groups (B0') to (B4').

Preferred are the combinations of the particular component (A) with one or more herbicides of group (B1'), (B2') or (B3').

Also preferred are the combinations (A)+(B1')+(B2'), (A)+(B1')+(B3') or (A)+(B2')+(B3').

The combinations according to the invention (=herbicidal compositions) have an outstanding herbicidal activity against a broad spectrum of economically important monocotyledonous and dicotyledonous harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Post-emergence application, or early post-sowing pre-emergence application, is preferred.

Specifically, examples may be mentioned of some representatives of the monocotyledonous and dicotyledonous weed flora which can be controlled by the compounds according to the invention, without the enumeration being a restriction to certain species. Examples of weed species on which the herbicidal compositions act efficiently are, from amongst the monocots, *Echinochloa* spp., *Setaria* spp., *Digitaria* spp., *Brachiaria* spp., *Panicum* spp., *Agropyron* spp., wild cereal forms and *Sorghum* spp., but also *Alopecurus* spp., *Avena* spp., *Apera spica venti*, *Lolium* spp. and *Phalaris* spp., *Poa* spp., and *Cyperus* species and *Imperata*.

In the case of the dicotyledonous weed species, the spectrum of action extends to species such as, for example, *Chenopodium* spp., *Amaranthus* spp., *Abutilon* spp., *Ipomoea* spp., *Polygonum* spp., *Xanthium* spp. and *Equisetum*, but also *Anthemis* spp., *Lamium* spp., *Matricaria* spp., *Stellaria* spp., *Kochia* spp., *Viola* spp., *Datura* spp., *Chrysanthemum* spp., *Thlaspi* spp., *Pharbitis* spp., *Sida* spp., *Sinapis* spp., *Cupsella* spp., *Ambrosia* spp., *Galium* spp., *Emex* spp., *Lamium* spp., *Papaver* spp., *Solanum* spp., *Cirsium* spp., *Veronica* spp., *Convolvulus* spp., *Rumex* and *Artemisia*.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

In comparison with the individual preparations, the herbicidal compositions according to the invention are distinguished by a more rapidly commencing and longer lasting herbicidal action. As a rule, the rainfastness of the active substances in the combinations according to the invention is advantageous. A particular advantage is that the dosages of the compounds (A) and (B), which are used in the combinations and are effective, can be adjusted to such a low quantity that their soil action is optimal. This does not only allow them to be employed in sensitive crops in the first place, but groundwater contaminations are virtually avoided. The active-substance-combination according to the invention allows the application rate of the active substances required to be reduced considerably.

When herbicides of the type (A)+(B) are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and grass weeds to be controlled, the herbicidal effect to take place more rapidly, the duration of action to be longer, the harmful plants to be controlled better while using only one, or few, applications, and the application period which is possible to be extended. In some cases, use of the compositions also reduces the amount of harmful constituents in the crop plant, such as nitrogen or oleic acid. The abovementioned properties and advantages are necessary under practical weed control conditions to keep agricultural crops free from undesired competing plants and thus to guarantee and/or increase the yields from the qualitative and quantitative point of view. These novel combinations markedly exceed the technical state of the art with a view to the properties described.

While the compounds according to the invention have an outstanding herbicidal activity against monocotyledonous and dicotyledonous weeds, the tolerant, or cross-tolerant, soybean plants are damaged only to a minor extent, or not at all.

Moreover, some of the compositions according to the invention have outstanding growth-regulatory properties on the soybean plants. They engage in the plants' metabolism in a regulatory manner and can thus be employed for provoking directed effects on plant constituents. Moreover, they are also suitable for the general control and inhibition of undesired vegetative growth without simultaneously destroying the plants. An inhibition of vegetative growth is very important in a large number of monocotyledonous and dicotyledonous crops since lodging can thus be reduced, or prevented completely.

Owing to their herbicidal and plant-growth-regulatory properties, the compositions can be employed for controlling harmful plants in known tolerant or cross-tolerant soybean crops, or in tolerant or genetically engineered soybean crops still to be developed. As a rule, the transgenic plants are distinguished by particular, advantageous properties, in addition to resistances to the compositions according to the invention, for example, by resistances to plant diseases or pathogens of plant diseases such as particular insects or microorganisms such as fungi, bacteria or viruses. Other particular properties relate, for example, to the harvested material with regard to quantity, quality, storability, composition and specific constituents. Thus, transgenic plants are known whose oil content is increased or whose quality is altered, for example where the harvested material has a different fatty acid composition.

Conventional methods of generating novel plants which have modified properties in comparison to plants occurring to date consist, for example, in traditional breeding methods and the generation of mutants. Alternatively, novel plants with altered properties can be generated with the aid of genetic engineering methods (see, for example, EP-A-0221044, EP-A-0131624). For example, the following were described in several cases:

the modification, by genetic engineering, of crop plants with the aim of modifying the starch synthesized in the plant (for example WO 92/11376, WO 92/14827, WO 91/19806), transgenic crop plants which exhibit resistances to other herbicides, for example to sulfonylureas (EP-A-0257993, U.S. Pat. No. 5,013,659), transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology with the aid of which novel transgenic plants with modified properties can be generated are known in principle; see, for example, Sambrook et al., 1989, Molecular Cloning, A Laboratory Manual, 2nd Edition, Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423–431.

To carry out such genetic engineering manipulations, nucleic acid molecules which allow mutagenesis or sequence changes by recombination of DNA sequences can be introduced in plasmids. For example, the abovementioned standard methods allow base changes to be carried out, subsequences to be removed, or natural or synthetic sequences to be added. To connect the DNA fragments to each other, adaptors or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use, on the one hand, DNA molecules which encompass the entire encoding sequence of a gene product inclusive of any flanking sequences which may be present, as well as DNA molecules which only encompass portions of the encoding sequence, it being necessary for these portions to be long enough to have an antisense effect on the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the encoding region with DNA sequences which ensure localization in a particular compartment. Such sequences are known to those skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give rise to whole plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

The invention therefore also relates to a method of controlling undesired vegetation in tolerant soybean crops, which comprises applying one or more herbicides of the type (A) and one or more herbicides of the type (B) to the harmful plants, parts of these plants, or the area under cultivation.

The invention also relates to the novel combinations of compounds (A)+(B) and to herbicidal compositions comprising them.

The active substance combinations according to the invention can exist not only as formulation mixes of the two components, if appropriate together with other active substances, additives and/or conventional formulation auxiliaries, which are then applied in the customary manner after dilution with water, but also as so-called tank mixes by jointly diluting the separately formulated, or partially separately formulated, components with water.

Compounds (A) and (B) or their combinations can be formulated in different ways, depending on the biological and/or chemico-physical parameters which prevail. The following are examples of general possibilities for formulations: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed-dressing materials, granules for soil application or for broadcasting, or water dispersible granules (WG), ULV formulations, microcapsules or waxes.

The individual formulation types are known in principle and are described, for example, in: Winnacker-Küchler "Chemische Technologie" [Chemical engineering], Volume 7, C. Hauser Verlag Munich, 4th Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y. Marsden, "Solvents Guide", 2nd Ed., Interscience, N.Y.

1950; McCutcheon's, "Detergents and Emulsifiers Annual", MC Publ. Corp., Ridegewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4th Edition 1986.

Based on these formulations, combinations with other pesticidally active substances, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active substance, also comprise ionic or non-ionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltauride, in addition to a diluent or inert material.

Emulsifiable concentrates are prepared by dissolving the active substance in an organic solvent, for example butanol, cyclohexanone, dimethylformamide, xylene or else higher-boiling aromatic or hydrocarbons with addition of one or more ionic or non-ionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active substance with finely divided solid materials, for example talc, natural clays such as kaolin, bentonite and pyrophyllite, or diatomateous earth.

Granules can be prepared either by spraying the active substance onto adsorptive, granulated inert material or by applying active substance concentrates to the surface of carriers such as sand, kaolites or granulated inert material with the aid of binders, for example polyvinyl alcohol, sodium polyacrylate or else mineral oils. Suitable active substances may also be granulated in the manner conventionally used for the production of fertilizer granules, if desired in a mixture with fertilizers. As a rule, water-dispersible granules are prepared by processes such as spray drying, fluidized-bed granulation, disk granulation, mixing with high-speed mixers and extrusion without solid inert material.

As a rule, the agrochemical preparations comprise 0.1 to 99 percent by weight, in particular 2 to 95% by weight, of active substances of the types A and/or B, the following concentrations being customary, depending on the type of formulation: The active substance concentration in wettable powders is, for example, approximately 10 to 95% by weight, the remainder to 100% by weight being composed of customary formulation constituents. In the case of emulsifiable concentrates, the active substance concentration may amount to, for example, 5 to 80% by weight.

Formulations in the form of dusts comprise, in most cases, 5 to 20% by weight of active substance, sprayable solutions approximately 0.2 to 25% by weight of active substance.

In the case of granules such as dispersible granules, the active substance content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active substance formulations may comprise, if appropriate, the conventional adhesives, wetters, dispersants, emulsifiers, preservatives, antifreeze agents, solvents, fillers, colors, carriers, antifoams, evaporation inhibitors, pH regulators or viscosity regulators.

For example, it is known that the effect of glufosinate-ammonium (A1.2) and of its L-enantiomer can be improved by surfactants, preferably by wetters from the series of the alkyl polyglycol ether sulfates which contain, for example, 10 to 18 carbon atoms and which are used in the form of their alkali metal salts or ammonium salts, but also as the magnesium salt, such as sodium $C_{12}/C_{14}$-fatty alcohol diglycol ether sulfate (®Genapol LRO, Hoechst); see EP-A-0476555, EP-A-0048436, EP-A-0336151 or U.S. Pat. No. 4,400,196 and Proc. EWRS Symp. "Factors Affecting Herbicidal Activity and Selectivity", 227–232 (1988). Moreover, it is known that alkyl polyglycol ether sulfates are also suitable as penetrants and synergists for a series of other herbicides, inter alia also herbicides from the series of the imidazolinones; see EP-A-0502014.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further prior to use with other inert substances.

The active substances can be applied to the plants, parts of the plants, seeds of the plants or the area under cultivation (soil of a field), preferably to the green plants and parts of the plants and, if appropriate, additionally to the soil of the field.

One possible use is the joint application of the active substances in the form of tank mixes, the concentrated formulations of the individual active substances, in optimal formulations, jointly being mixed with water in the tank and the resulting spray mixture being applied.

A joint herbicidal formulation of the combination according to the invention of the active substances (A) and (B) has the advantage of being easier to apply since the quantities of the components are already presented in the correct ratio to each other. Moreover, the adjuvants in the formulation can be matched optimally to each other, while a tank mix of different formulations may lead to undesired combinations of adjuvants.

A. General Formulation Examples a) A dust is obtained by mixing 10 parts by weight of an active substance/active substance mixture and 90 parts by weight of talc as inert material and comminuting the mixture in a hammer mill.

b) A wettable powder which is readily dispersible in water is obtained by mixing 25 parts by weight of an active substance/active substance mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active substance/active substance mixture with 6 parts by weight of alkylphenol polyglycol ether (®Triton X 207), 3 parts by weight of isotridecanol polyglycol ether (8 EO)

and 71 parts by weight of paraffinic mineral oil (boiling range for example approx. 255 to 277 C), and grinding the mixture in a ball mill to a fineness of below 5 microns.
d) An emulsifiable concentrate is obtained from 15 parts by weight of an active substance/active substance mixture, 75 parts by weight of cyclohexanone as solvent and 10 parts by weight of oxethylated nonylphenol as emulsifier.
e) Water-dispersible granules are obtained by mixing
   75 parts by weight of an active substance/active substance mixture,
   10 parts by weight of calcium lignosulfonate,
   5 parts by weight of sodium lauryl sulfate,
   3 parts by weight of polyvinyl alcohol and
   7 parts by weight of kaolin,
   grinding the mixture on a pinned-disk mill and granulating the powder in a fluidized bed by spraying on water as granulation liquid.
f) Water-dispersible granules are also obtained by homogenizing and precomminuting, on a colloid mill,
   25 parts by weight of an active substance/active substance mixture,
   5 parts by weight of sodium 2,2'-dinaphthylmethane-6,6'-disulfonate,
   2 parts by weight of sodium oleoylmethyltaurinate,
   1 part by weight of polyvinyl alcohol,
   17 parts by weight of calcium carbonate and
   50 parts by weight of water,
   subsequently grinding the mixture in a bead mill and atomizing and drying the resulting suspension in a spray tower by means of a single-substance model.

Biological Examples

1. Pre-emergence Effect on Weeds

Seeds or rhizome pieces of monocotyledonous and dicotyledonous weed plants are placed in sandy loam soil in plastic pots and covered with soil. The compositions which are formulated in the form of concentrated aqueous solutions, wettable powders or emulsion concentrates are then applied to the surface of the soil cover in the form of an aqueous solution, suspension or emulsion at an application rate of 600 to 800 l of water/ha (converted), in various dosages. After the treatment, the pots are placed in a greenhouse and kept under good growth conditions for the weeds. After the test plants have emerged, the damage to the plants or the negative effect on the emergence is scored visually after a test period of 3 to 4 weeks by comparison with untreated controls. As shown by the test results, the compositions according to the invention have a good herbicidal pre-emergence activity against a broad spectrum of grass weeds and dicotyledonous weeds.

Frequently, effects of the combinations according to the invention are observed which exceed the formal total of the effects when applying the herbicides individually (=synergistic effect).

If the data of the effects observed already exceed the formal total ($=E^A$) of the data of the experiments with individual applications, then they also exceed Colby's expected value ($=E^C$), which is calculated by the formula which follows and which is also considered to be suggestive of synergism (cf. S. R. Colby; in Weeds 15 (1967) pp. 20 to 22):

$$E = A + B - (A \cdot B/100)$$

A, B denote the effect of th active substances A, or in %, for a or b g of a.s./ha; E denotes the expected value in % for a+b g a.s./ha.

At suitable low dosages, the observed data of the experiments show an effect of the combinations above Colby's expected values.

2. Post-emergence Effect on Weeds

Seeds or rhizome pieces of monocotyledonous and dicotyledonous weeds are placed in sandy loam soil in cardboard pots, covered with soil and grown in the greenhouse under good growth conditions. Three weeks after sowing, the test plants in the three-leaf stage are treated with the compositions according to the invention. The compositions according to the invention which are formulated as wettable powders or as emulsion concentrates are sprayed in various dosages on the green parts of the plants at an application rate of 600 to 800 l of water/ha (converted). After the test plants have remained in the greenhouse for about 3 to 4 weeks under optimal growth conditions, the effect of the products is scored visually by comparison with untreated controls. When applied post-emergence, too, the compositions according to the invention have a good herbicidal activity against a broad spectrum of economically important grass weeds and broad-leaved weeds.

Frequently, effects of the combinations according to the invention are observed which exceed the formal total of the effects when applying the herbicides individually. At suitable low dosages, the observed data of the experiments show an effect of the combinations above Colby's expected values. (cf. score figures in Example 1).

3. Herbicidal Effect and Tolerance by Crop Plants (Field Trial)

Transgenic soybean plants with a resistance to one or more herbicides (A) together with typical weed plants were grown in the open on 2×5 m plots under natural field conditions; alternatively, weed infestation occurred naturally when the soybean plants were grown. The treatment with the compositions according to the invention and, as control, separately by only applying the active substances of the components, was carried out under standard conditions with a plot sprayer at an application rate of 200–300 liters of water per hectare in parallel tests as can be seen from the scheme in Table 1, i.e. pre-sowing pre-emergence, post-sowing pre-emergence or post-emergence in the early, medium or late stage.

TABLE 1

Use scheme - examples

| Application of the active substances | Pre-sowing | Pre-emergence post-sowing | Post-emergence 1-2-leaf | Post-emergence 2-4-leaf | Post-emergence 6-leaf |
|---|---|---|---|---|---|
| Combination | (A) + (B) | | | | |
| " | | (A) + (B) | | | |
| " | | | (A) + (B) | | |
| " | | | | (A) + (B) | |
| " | | | | | (A) + (B) |
| Sequential | (A) + (B) | (A) + (B) | | | |
| " | | (A) + (B) | (A) + (B) | | |
| " | (A) | (A) + (B) | | | |
| " | (B) | (A) + (B) | | | |
| " | | | (A) + (B) | (A) + (B) | |
| " | | | (A) + (B) | (A) + (B) | (A) + (B) |
| " | (B) | | (A) | (A) + (B) | |
| " | | (B) | | (A) + (B) | (A) + (B) |
| " | | | | (A) + (B) | (A) + (B) |
| " | | | (A) | (A) + (B) | (A) + (B) |

2, 4, 6 and 8 weeks after the application, the herbicidal activity of the active substances or active substance mixtures was scored visually with reference to the treated plots in comparison to untreated control plots. The damage to, and the development of, all aerial parts of the plants was recorded. Scoring was done on the basis of a percentage sale (100% action all plants destroyed; 50% action=50% of the plants and green parts of the plants destroyed; 0% action=no recognizable effect=like control plot. The mean of the score values of in each case 4 plots was calculated.

The comparison demonstrated that the herbicidal effect of the combinations according to the invention was usually higher, in some cases considerably higher, than the total of the effects of the individual herbicides. In essential periods of the period of scoring, the effects were greater than Colby's expected values (cf. scoring in Example 1) and therefore suggest a synergism. In contrast, the soybean plants were not damaged owing to the treatments with the herbicidal compositions, or were only damaged to a negligible extent.

Abbreviations generally used in the following tables:

| | |
|---|---|
| g of a.s./ha = | gram of active substance (100% active substance) per hectare |
| $E^A$ = | Total of the herbicidal effects of the individual applications |
| $E^C$ = | Colby's expected value (cf. scoring in Table 1) |
| Soybean LL = | glufosinate-tolerant soybean culture, |

TABLE 2

Herbicidal effect in field trials with soybeans

| Active substance(s) | Dose[1] g of a.s./ha | Herbicidal action[2] (%) against Equisetum arvense |
|---|---|---|
| (A1.2) | 400 | 70 |
| (B2.5) | 150 | 0 |
| | 300 | 0 |
| (A1.2) + (B2.5) | 400 + 150 | 75 |

Abbreviations for Table 2:
[1]Application in the 4–6 leaf stage
[2]Scoring 3 weeks after application
(A1.2) = glufosinate-ammonium
(B2.5) = lactofen

TABLE 3

Herbicidal effect in field trials with soybeans

| Active substance(s) | Dose[1] g of a.s./ha | Herbicidal action[2] (%) against Digitalis abscendens |
|---|---|---|
| (A1.2) | 1200 | 36 |
| (B1.8) | 2580 | 48 |
| (A1.2) + (B1.8) | 1200 + 2580 | 75 (E = 58) |

Abbreviations for Table 3:
[1]Application middle-end of stocking
[2]Scoring 3 weeks after application
(A1.2) = glufosinate-ammonium
(B1.8) = alachlor The treated soybean crop showed no significant damage.

TABLE 4

Herbicidal effect in field trials with soybeans

| Active substance(s) | Dose[1] g of a.s./ha | Herbicidal action[2] (%) against Sorghum sudaneus |
|---|---|---|
| (A1.2) | 500 | 65 |
| | 300 | 15 |
| (B1.9) | 750 | 15 |
| (A1.2) + (B1.9) | 300 + 750 | 73 ($E^A$ = 30) |
| (B2.8) | 360 | 15 |
| (A1.2) + (B2.8) | 300 + 360 | 70 ($E^A$ = 30) |
| (B2.3) | 15 | 13 |
| (A1.2) + (B2.3) | 300 + 15 | 33 ($E^A$ = 30) |

Abbreviations for Table 4:
[1]Application in the 4-leaf stage
[2]Scoring 28 days after application
(A1.2) = glufosinate-ammonium
(B2.1) = linuron
(B2.8) = aciflurofen
(B2.3) = thifensulfuron-methyl

TABLE 5

Herbicidal effect in field trials with soybeans

| Active substance(s) | Dose[1] g of a.s./ha | Herbicidal action[2] (%) against Portulaca oleracea | Soja LL |
|---|---|---|---|
| (A1.2) | 500 | 65 | 0 |
| | 250 | 20 | 0 |
| (B2.12) | 18 | 73 | 2 |
| (A1.2) + (B2.12) | 250 + 18 | 95 ($E^A$ = 93) | 3 |
| (B1.15) | 100 | 65 | 0 |
| (A1.2) + (B1.15) | 250 + 100 | 99 ($E^A$ = 85) | 0 |
| (B1.5) | 2240 | 30 | 0 |
| (A1.2) + (B1.5) | 250 + 2240 | 78 ($E^A$ = 50) | 0 |
| (B2.3) | 5 | 45 | 3 |
| (A1.2) + (B2.3) | 250 + 5 | 73 (E = 65) | 4 |

Abbreviations for Table 5:
[1]Application in the 8–10 leaf stage
[2]Scoring 32 days after application
(A1.2) = glufosinate-ammonium
(B2.12) = cloransulam-methyl
(B1.15) = flumioxazin
(B1.5) = metolachlor
(B2.3) = thifensulfuron-methyl

TABLE 6

Herbicidal effect in field trials with soybeans

| Active substance(s) | Dose[1] g of a.s./ha | Herbicidal action[2] (%) against Eleusine indica | Soja LL |
|---|---|---|---|
| (A1.2) | 500 | 80 | 0 |
| | 200 | 40 | 0 |
| (B4.2) | 25 | 30 | 0 |
| | 50 | 70 | 0 |
| (A1.2) + (B4.2) | 200 + 25 | 83 ($E^A$ = 70) | 0 |
| (A3.2) | 50 | 27 | 0 |
| (A1.2) + (A3.2) | 200 + 50 | 73 ($E^A$ = 67) | 0 |
| (B2.11) | 12.5 | 5 | 0 |
| (A1.2) + (B2.11) | 200 + 12.5 | 63 ($E^A$ = 45) | 0 |
| (B4.4) | 60 | 45 | 0 |
| (A1.2) + (B4.4) | 200 + 60 | 93 ($E^A$ = 85) | 0 |

Abbreviations for Table 6:
[1]Application in th 3-leaf stage
[2]Scoring 42 days after application
(A1.2) = glufosinate-ammonium
(B4.2) = fenoxaprop-P-ethyl
(A3.2) = imazethapyr
(B2.11) = chlorimuron
(B4.4) = haloxyfop-P-methyl

TABLE 7

Herbicidal effect in field trials with soybeans

| Active substance(s) | Dose[1] g of a.s./ha | Herbicidal action[2] (%) against Pharbitis purpureum | Soja LL |
|---|---|---|---|
| (A1.2) | 400 | 72 | 0 |
|  | 200 | 35 | 0 |
| (B2.12) | 40 | 45 | 0 |
| (A1.2) + (B2.12) | 200 + 40 | 85 ($E^A$ = 80) | 0 |
| (B1.15) | 12.5 | 30 | 0 |
| (A1.2) + (B1.15) | 200 + 12.5 | 78 ($E^A$ = 65) | 0 |
| (A3.5) | 30 | 40 | 0 |
| (A1.2) + (A3.5) | 200 + 30 | 77 ($E^A$ = 75) | 0 |
| (B2.2) | 480 | 35 | 0 |
| (A1.2) + (B2.2) | 200 + 480 | 80 ($E^A$ = 70) | 0 |

Abbreviations for Table 7:
[1] Application in the 3-leaf stage
[2] Scoring 42 days after application
(A1.2) = glufosinate-ammonium
(B2.12) = cloransulam-methyl
(B1.15) = flumioxazin
(B1.5) = metolachlor
(A3.5) = imazamox
(B2.2) = bentazone

TABLE 8

Herbicidal effect in field trials with soybeans

| Active substance(s) | Dose[1] g of a.s./ha | Herbicidal action[2] (%) against Sida rombifolia | Soja LL |
|---|---|---|---|
| (A1.2) | 300 | 65 | 0 |
|  | 150 | 25 | 0 |
| (B2.7) | 50 | 40 | 0 |
| (A1.2) + (B2.7) | 150 + 50 | 83 ($E^A$ = 65) | 0 |
| (B2.15) | 50 | 60 | 0 |
| (A1.2) + (B2.15) | 150 + 50 | 93 ($E^A$ = 85) | 0 |

Abbreviations for Table 8:
[1] Application in the 4-leaf stage
[2] Scoring 43 days after application
(A1.2) = glufosinate-ammonium
(B2.7) = flumiclorac-pentyl
(B2.15) = oxasulfuron

TABLE 9

Herbicidal effect in field trials with soybeans

| Active substance(s) | Dose[1] g of a.s./ha | Herbicidal action[2] (%) against Xanthium orientalis |
|---|---|---|
| (A1.2) | 500 | 98 |
|  | 300 | 96 |
| (B1.1) | 960 | 0 |
| (A1.2) + (B1.1) | 300 + 960 | 99 ($E^A$ = 96) |

Abbreviations for Table 9:
[1] Application in the 5-leaf stage
[2] Scoring 28 days after application
(A1.2) = glufosinate-ammonium
(B1.1) = trifluralin

TABLE 10

Herbicidal effect in field trials with soybeans

| Active substance(s) | Dose[1] g of a.s./ha | Herbicidal action[2] (%) against Abutilon theophrasti |
|---|---|---|
| (A1.2) | 500 | 95 |
|  | 330 | 45 |
| (B2.5) | 2240 | 20 |
| (A1.2) + (B1.5) | 330 + 2240 | 67 ($E^A$ = 65) |
| (B1.7) | 1500 | 30 |
| (A1.2) + (B1.7) | 330 + 1500 | 83 ($E^A$ = 75) |
| (B1.6) | 35 | 52 |
| (A1.2) + (B1.6) | 330 + 35 | 99 ($E^A$ = 92) |
| (B4.4) | 500 | 50 |
| (A1.2) + (B4.4) | 330 + 500 | 99 (E = 95) |

Abbreviations for Table 10:
[1] Application in the 4-leaf stage
[2] Scoring 42 days after application
(A1.2) = glufosinate-ammonium
(B1.5) = metolachlor
(B1.7) = dimethenamid
(B1.6) = flumetsulam
(B4.4) = sulfentrazone

The invention claimed is:
1. A method of controlling harmful plants in soybean crops, comprising applying jointly or separately, pre-emergence, post-emergence or pre- and post-emergence to the plants, parts of the plants, seeds of the plants or the area under cultivation a synergistic effective amount of a herbicidal combination comprising:
(A) a broad-spectrum herbicide selected from the group consisting of:
(A1) compounds of the formula (A1),

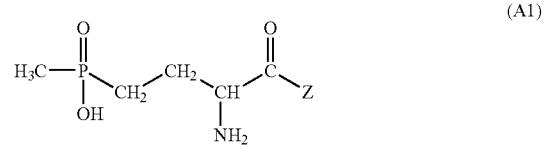

(A1)

wherein Z is a radical of the formula —OH or a peptide radical of the formula —NHCH(CH$_3$)CONHCH(CH$_3$)COOH or —NHCH(CH$_3$)CONHCH[CH$_2$CH(CH$_3$)$_2$]COOH, and their esters and salts and other phosphinothricin derivatives,
(A2) compounds of the formula (A2) and their salts,

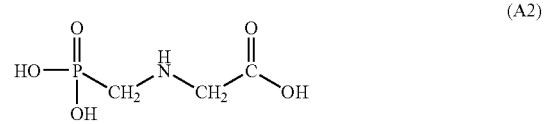

(A2)

(A3) imidazolinones and their salts and
(A4) herbicidal azoles from the protoporphyrinogen-oxidase inhibitors (PPO inhibitors) and
(B) one or more herbicides selected from the group consisting of:
(B1) foliar-acting and/or soil-acting herbicides which are effective selectively in soybeans against monocotyledonous and predominantly dicotyledonous harmful plants, selected from the group consisting of trifluralin, metribuzin, clomazone, pendimethalin, metolachlor, flumetsulam, dimethenamid, alachlor, linuron, sulfentrazone, ethalfluralin, fluthiamide, norflurazone, vernolate and flumioxazin,
(B2) herbicides which are effective selectively in soybeans against dicotyledonous harmful plants, selected from the group consisting of chlortoluron, bentazone, thifensulfuron, oxyfluorfen, lactofen, fomesafen, flumiclorac, acifluorfen, 2,4-DB, 2,4-D, chlorimuron, diclosulam, fluthiacet, cloransulam and oxasulfuron,
(B3) foliar- and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, haloxyfop-P and propaquizafop or
(B5) nonselective herbicides which can be employed in soybeans for specific purposes, selected from the group consisting of paraquat or
and optionally at least one safener,
whereby the soybean crops are tolerant to the herbicides (A) and (B) which form a constituent of the combination, with the exception of the following combinations:
a) combinations comprising compounds of group (A1) and compounds of group (B) selected from the group consisting of cloransulam, metolachlor, metribuzin, chlorimuron, dimethenamid, pendimethalin, bentazone, clomazone, thifensulfuron, flumiclorac, flumetsulam, linuron, sethoxydim, acifluorfen, fomesafen, sulfentrazone, flumioxazin, lactofen, norflurazone, propaquizafop, fenoxaprop-P, fluthiacet and oxasulfuron;
b) combinations comprising compounds of group (A2) and compounds of group (B) selected from the group consisting of metolachlor, dimethenamid, metribuzin, chlorimuron, pendimethalin, bentazone, linuron, norflurazone, propaquizafop, acifluorfen, fluthiacet and oxasulfuron;
c) combinations comprising compounds of group (A3) from the group consisting of imazethapyr, and compounds of group (B) from the group consisting of 2,4-D, metolachlor, bentazone, clomazone, thifensulfuron, flumiclorac, pendimethalin trifluralin, sulfentrazone, lactofen, dimethenamid, acifluorfen and fenoxaprop-P;
d) combinations comprising compounds of group (A3) selected from the group consisting of 2,4-D, imazaquin, and compounds of group (B) selected from the group consisting of pendimethalin, trifluralin and metolachlor;
e) combinations comprising compounds of group (A3) selected from the group consisting of imazamox (AC299263), and compounds of group (B) selected from the group consisting of bentazone and trifluralin;
f) combinations comprising compounds of group (A3) selected from the group consisting of imazapyr, and compounds of group (B) selected from the group consisting of metolachlor.

2. The method according to claim 1, wherein the herbicide (A) is glufosinate-ammonium.

3. The method according to claim 1, wherein the herbicide (A) is glyphosate-isopropylammonium.

4. The method according to claim 1, wherein the herbicide (B) is selected from the group consisting of:

(B1) foliar-acting and/or soil-acting herbicides which are effective selectively in soybeans against monocotyledonous and predominantly dicotyledonous harmful plants, selected from the group consisting of trifluralin, flumetsulam, alachlor, ethalfluralin, fluthiamide and vernolate,
(B2) chlortolurondiclosulam,
(B3) foliar- and soil-acting herbicides which are effective selectively in soybeans against monocotyledonous harmful plants, selected from the group consisting of cycloxydim and clethodim,
(B4) foliar-acting herbicides which are effective selectively in soybeans against monocotyledonous harmful plants, selected from the group consisting of quizalofop-P, quizalofop, fluazifop-P, fluazifop, haloxyfop and haloxyfop-P or
(B5) nonselective herbicides which can be employed in soybeans for specific purposes, selected from the group consisting of paraquat or
a mixture of herbicides selected from groups (B0) to (B4).

5. The method according to claim 1, wherein the herbicidal combination further comprises other crop protection agents.

6. The method according to claim 1, wherein the herbicidal combination further comprises adjuvants and formulation auxiliaries conventionally used in crop protection.

7. A synergistic herbicidal combination, comprising a synergistic effective amount consisting of:
one or more herbicides of group (A4) selected from the group consisting of herbicidal azoles from the protoporphyrinogen-oxidase inhibitors (PPO inhibitors) and of one or more herbicides of group (B) according to claim 1.

8. A method for regulating the growth of soybean plants, comprising applying a synergistically effective amount of a synergistic herbicidal combination according to claim 7 to said plants.

9. The method according to claim 8, wherein the yield on constituents of soybean plants are influenced.

10. A synergistic herbicidal combination, comprising a synergistic effective amount consisting of glyphosate-isopropylammonium and one or more herbicides selected from the group consisting of:

(B1) foliar-acting and/or soil-acting herbicides which are effective selectively in soybeans against monocotyledonous and predominantly dicotyledonous harmful plants, selected from the group consisting of flumetsulam, alachlor, ethalfluralin, vernolate and flumioxazin,
(B2') herbicides which are effective selectively in soybeans against dicotyledonous harmful plants, selected from the group consisting of chlortoluron, oxyfluorfen, lactofen, fomesafen, flumiclorac, and diclosulam,
(B3') foliar- and soil-acting herbicides which are effective selectively in soybeans against monocotyledonous harmful plants, selected from the group consisting of sethoxydim, cycloxydim and clethodim,
(B4') foliar-acting herbicides which are effective selectively in soybeans against monocotyledonous harmful plants, selected from the group consisting of quizalofop-P, and quizalofop, or
(B5') nonselective herbicides which can be employed in soybeans for specific purposes, selected from the group consisting of paraquat
or a mixture of herbicides from groups (B1') to (B4') and, optionally, adjuvants or formulation auxiliaries conventionally used in crop protection.

11. A method for regulating the growth of soybean plants, comprising applying a synergistically effective amount of a synergistic herbicidal combination according to claim 10 to said plants.

12. The method according to claim 11, wherein the yield on constituents of soybean plants are influenced.

13. A synergistic herbicidal combination, comprising a synergistic effective amount consisting of glufosinate-ammonium and one or more herbicides selected from the group consisting of:
- (B1') foliar-acting and/or soil-acting herbicides which are effective selectively in soybeans against monocotyledonous and predominantly dicotyledonous harmful plants, selected from the group consisting of alachlor, ethalfluralin, and vernolate,
- (B2') herbicides which are effective selectively in soybeans against dicotyledonous harmful plants, from the group consisting of chlortoluron and diclosulam,
- (B3') foliar- and soil-acting herbicides which are effective selectively in soybeans against monocotyledonous harmful plants, selected from the group consisting of cycloxydim and clethodim,
- (B4') foliar-acting herbicides which are effective selectively in soybeans against monocotyledonous harmful plants, selected from the group consisting of quizalofop-P, quizalofop, haloxyfop and haloxyfop-P or
- (B5') nonselective herbicides which can be employed in soybeans for specific purposes, selected from the group consisting of paraquat
- or a mixture of herbicides selected from groups (B1') to (B5') and, optionally, adjuvants or formulation auxiliaries conventionally used in crop protection.

14. A method for regulating the growth of soybean plants, comprising applying a synergistically effective amount of a synergistic herbicidal combination according to claim 13 to said plants.

15. The method according to claim 14, wherein the yield on constituents of soybean plants are influenced.

16. A method of controlling harmful plans in soybean crops, comprising applying jointly or separately, pre-emergence, post-emergence or pre- and post-emergence to the plants, parts of the plants, seeds of the plants or the area under cultivation a synergistic effect amount of a herbicidal combination comprising:
- (A) a broad-spectrum herbicide from the group of the compounds consisting of:
- (A1) compounds of the formula (A1),

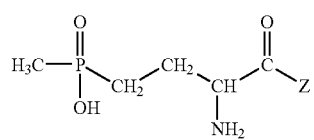

in which Z is a radical of the formula —OH or a peptide radical of the formula —NHCH(CH$_3$)CONHCH (CH$_3$)COOH or —NHCH(CH$_3$)CONHCH[CH$_2$CH (CH$_3$)$_2$]COOH, and their esters and salts and other phosphinothricin derivatives, and

- (B) one or more herbicides selected from the group consisting of:
- (B1) foliar-acting and/or soil-acting herbicides which are effective selectively in soybeans against monocotyledonous and predominantly dicotyledonous harmful plants, selected from the group consisting of trifluralin, alachlor, ethalfluralin, fluthiamide, vernolate,
- (B2) herbicides which are effective selectively in soybeans against dicotyledonous harmful plants, from the group consisting of chlortoluron, oxyfluorfen, 2,4-DB, 2,4-D, diclosulam,
- (B3) foliar- and soil-acting herbicides which are effective selectively in soybeans against monocotyledonous harmful plants, from the group consisting of cycloxydim and clethodim,
- (B4) foliar-acting herbicides which are effective selectively in soybeans against monocotyledonous harmful plants, from the group consisting of quizalofop-P, quizalofop, fenoxaprop, fluazifop-P, fluazifop, haloxyfop, and haloxyfop-P or
- (B5) nonselective herbicides which can be employed in soybeans for specific purposes, from the group consisting of paraquat or
- and optionally at least one safener, whereby the soybean crops are tolerant to the herbicides (A) and (B) which form a constituent of the combination.

17. The method according to claim 16, wherein the herbicide (A) is glufosinate-ammonium.

18. The method according to claim 16, wherein the herbicide (B) is selected form the group of:
- (B1) foliar-acting and/or soil-acting herbicides which are effectively selectively in soybeans against monocotyledonous and predominantly dicotyledonous harmful plants, from the group consisting of trifluralin, alachlor, ethalfluralin, fluthiamide and vernolate,
- (B2) herbicides which are effective selectively in soybeans against dicotyledonous harmful plants, from the group consisting of chlortoluron and diclosulam,
- (B3) foliar- and soil-acting herbicides which are effective selectively in soybeans against monocotyledonous harmful plants, from the group consisting of cycloxydim and clethodim,
- (B4) foliar-acting herbicides which are effective selectively in soybeans against monocotyledonous harmful plants, from the group consisting of quizalofop-P, quizalofop, fluazifop-P, fluazifop, haloxyfop and haloxyfop-P or
- (B5) nonselective herbicides which can be employed in soybeans for specific purposes, from the group consisting of paraquat or a mixture of herbicides selected from groups (B1) to (B5).

19. The method according to claim 16, wherein the herbicidal combination further comprises other crop protection agents.

20. The method according to claim 16, wherein the herbicidal combination further comprises adjuvants and formulation auxiliaries conventionally used in crop protection.

* * * * *

UNITED STATES PATENT AND TRADEMARK OFFICE
CERTIFICATE OF CORRECTION

PATENT NO. : 7,105,470 C1
APPLICATION NO. : 90/009711
DATED : July 31, 2012
INVENTOR(S) : Hacker et al.

It is certified that error appears in the above-identified patent and that said Letters Patent is hereby corrected as shown below:

Please delete Patent 7,105,470C1 in its entirety and substitute Patent 7,105,470C1 in its entirety as attached.

Signed and Sealed this
Twenty-eighth Day of May, 2013

Teresa Stanek Rea
*Acting Director of the United States Patent and Trademark Office*

(12) EX PARTE REEXAMINATION CERTIFICATE (9160th)
United States Patent
Hacker et al.

(10) Number: US 7,105,470 C1
(45) Certificate Issued: Jul. 31, 2012

(54) HERBICIDAL COMPOSITIONS FOR TOLERANT OR RESISTANT SOYBEAN CROPS

(75) Inventors: Erwin Hacker, Hochheim (DE);
Hermann Bieringer, Eppstein (DE);
Lothar Willms, Hofheim (DE)

(73) Assignee: Bayer Cropscience AG, Monheim (DE)

Reexamination Request:
No. 90/009,711, Mar. 26, 2010

Reexamination Certificate for:
Patent No.: 7,105,470
Issued: Sep. 12, 2006
Appl. No.: 09/371,612
Filed: Aug. 10, 1999

(51) Int. Cl.
*A01N 57/02* (2006.01)
*A01N 43/42* (2006.01)
*A01N 43/52* (2006.01)
*A01N 57/20* (2006.01)
*A01P 13/00* (2006.01)

(52) U.S. Cl. ............ 504/127; 504/128; 504/139; 504/145; 504/132; 504/130

(58) Field of Classification Search .................. None
See application file for complete search history.

(56) References Cited

PUBLICATIONS

To view the complete listing of prior art documents cited during the proceeding for Reexamination Control Number 90/009,711, please refer to the USPTO's public Patent Application Information Retrieval (PAIR) system under the Display References tab.

*Primary Examiner* – Bruce Campell

(57) ABSTRACT

Herbicide combinations (A)+(B), if appropriate in the presence of safeners, with an effective content of (A) broad-spectrum herbicides from the group (A1) glufosinate (salts) and related compounds (A2) glyphosate (salts) and related compounds such as sulfosate, (A3) imidazolinones such as imazethapyr, imazapyr, imazaquin, imazamox or their salts and (A4) herbicidal azoles from the group of the protoporphyrinogen oxidase inhibitors (PPO inhibitors) and (B) one or more herbicides from the group of the compounds consisting of (B0) one or more structurally different herbicides from the above-mentioned group (A) and/or (B1) foliar- and/or soil-acting herbicides (residual action) which are effective selectively in soybeans against monocotyladonous and predominantly dicotyledonous harmful plants or (B2) herbicides which are effective selectively in soybeans against dicotyledonous harmful plants, or (B3) foliar- and soil-acting herbicides which are effective selectively in soybeans against monocotyledonous harmful plants or (B4) foliar-acting herbicides which are effective selectively in soybeans against monocotyledonous and dicotyledonous harmful plants or (B5) nonselective herbicides which can be employed in soybeans for specific purposes, such as paraquat (salts), or herbicides from several of groups (B0) to (B5)

are suitable for controlling harmful plants in soybeans which consists of tolerant or resistant mutants or transgenic soybean plants and the soybean crops are tolerant to the herbicides (A) and (B), if appropriate in the presence of safeners, which are contained in the combination.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13-15 is confirmed.

Claims 1, 4, 10 and 16 are determined to be patentable as amended.

Claims 2, 3, 5, 6, 11, 12, 17-20, dependent on an amended claim, are determined to be patentable.

New claims 21-101 are added and determined to be patentable.

Claims 7-9 were not reexamined.

1. A method of controlling harmful plants in soybean crops, comprising applying jointly or separately, pre-emergence, post-emergence or pre- and post- emergence to the plants, parts of the plants, seeds of the plants or the area under cultivation a synergistic effective amount of a herbicidal combination comprising:
   (A) a broad-spectrum herbicide selected from the group consisting of:
   (A1) compounds of the formula (A1),

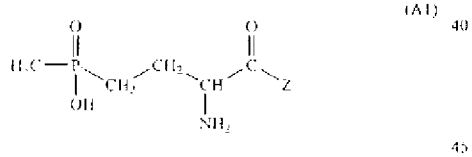

wherein Z is a radical of the formula -OH or a peptide radical of the formula -NHCH(CH₃)CONHCH(CH₃)COOH or -NHCH(CH₃)CONHCH[CH₂CH(CH₃)₂]COOH, and their esters and salts and other phosphinothricin derivatives,
   (A2) compounds of the formula (A2) and their salts,

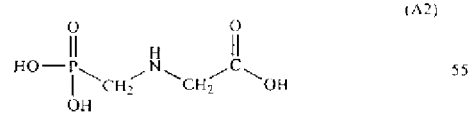

(A3) imidazolinones and their salts and
   (A4) herbicidal azoles from the protoporphyrinogen-oxidase inhibitors (PPO inhibitors) and
   (B) one or more herbicides selected from the group consisting of:
      (B1) foliar-acting and/or soil-acting herbicides which are effective selectively in soybeans against monocotyledonous and predominantly dicotyledonous harmful plants, selected from the group consisting of trifluralin, metribuzin, clomazone, pendimethalin, metolachlor, flumetsulam, dimethenamid, alachlor, linuron, sulfentrazone, ethalfluralin, fluthiamide, norflurazone, vernolate and flumioxazin,
      (B2) herbicides which are effective selectively in soybeans against dicotyledonous harmful plants, selected from the group consisting of chlortoluron, bentazone, thifensulfuron, oxyfluorfen, lactofen, fomesafen, flumiclorac, acifluorfen, 2,4-DB, [2,4-D,] chlorimuron, diclosulam, fluthiacet, cloransulam and oxasulfuron,
      (B3) foliar- and soil-acting herbicides which are effective selectively in soybeans against monocotyledonous harmful plants, selected from the group consisting of sethoxydim, cycloxydim and clethodim,
      (B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, haloxyfop-P and propaquizafop or
      (B5) nonselective herbicides which can be employed in soybeans for specific purposes, selected from the group consisting of paraquat or
   and optionally at least one safener,
   whereby the soybean crops are tolerant to the herbicides (A) and (B) which form a constituent of the combination, with the exception of the following combinations:
   combinations comprising compounds of group (A1) and compounds of group (B) selected from the group consisting of cloransulam, metolachlor, metribuzin, chlorimuron, dimethenamid, pendimethalin, bentazone, clomazone, thifensulfuron, flumiclorac, flumetsulam, linuron, sethoxydim, acifluorfen, fomesafen, sulfentrazone, flumioxazin, lactofen, norflurazone, propaquizafop, fenoxaprop-P, fluthiacet and oxasulfuron;
   combinations comprising compounds of group (A2) and compounds of group (B) selected from the group consisting of metolachlor, dimethenamid, metribuzin, chlorimuron, pendimethalin, *flumetsulam, sulfentrazone, thifensulfuron, lactofen,* bentazone, linuron, norflurazone, propaquizafop, acifluorfen, fluthiacet *sethoxydim, quizalofop* and oxasulfuron;
   combinations comprising compounds of group (A3) from the group consisting of imazethapyr, and compounds of group (B) from the group consisting of [2,4-D,] metolachlor, bentazone, clomazone, thifensulfuron, flumiclorac, pendimethalin, trifluralin, sulfentrazone, lactofen, dimethenamid, acifluorfen and fenoxaprop-P;
   combinations comprising compounds of group (A3) selected from the group consisting of [2,4-D,] imazaquin, and compounds of group (B) selected from the group consisting of pendimethalin, trifluralin and metolachlor;
   combinations comprising compounds of group (A3) selected from the group consisting of imazamox (AC299263), and compounds of group (B) selected from the group consisting of bentazone and trifluralin;
   combinations comprising compounds of group (A3) selected from the group consisting of imazapyr, and compounds of group (B) selected from the group consisting of metolachlor.

4. The method according to claim 1, wherein the herbicide (B) is selected from the group consisting of:
- (B1) foliar-acting and/or soil-acting herbicides which are effective selectively in soybeans against monocotyledonous and predominantly dicotyledonous harmful plants, selected from the group consisting of trifluralin, flumetsulam, alachlor, ethalfluralin, fluthiamide and vernolate, [(B2) chlortolurondiclosulam,]
- (*B2*) *chlortoluron and diclosulam;*
- (B3) foliar- and soil-acting herbicides which are effective selectively in soybeans against monocotyledonous harmful plants, selected from the group consisting of cycloxydim and clethodim,
- (B4) foliar-acting herbicides which are effective selectively in soybeans against monocotyledonous harmful plants, selected from the group consisting of quizalofop-P, quizalofop, fluazifop-P, fluazifop, haloxyfop and haloxyfop-P or
- (B5) nonselective herbicides which can be employed in soybeans for specific purposes, selected from the group consisting of paraquat or
- [a mixture of herbicides selected from groups (B0) to (B4)] *a mixture of herbicides selected from the groups consisting of (B1) to (B5)*.

10. A synergistic herbicidal combination, comprising a synergistic effective amount consisting of glyphosate-isopropylammonium and one or more herbicides selected from the group consisting of:
- (B1') foliar-acting and/or soil-acting herbicides which are effective selectively in soybeans against monocotyledonous and predominantly dicotyledonous harmful plants, selected from the group consisting of [flumetsulam, alachlor, ethalfluralin, vernolate and flumioxazin] *alachlor, ethalfluralin, vernolate and flumioxazin*,
- (B2') herbicides which are effective selectively in soybeans against dicotyledonous harmful plants, from the group consisting of chlortoluron, oxyfluorfen, [lactofen, fomesafen,] flumiclorac and diclosulam,
- (B3') foliar- and soil-acting herbicides which are effective selectively in soybeans against monocotyledonous harmful plants, selected from the group consisting of [sethoxydim,] cycloxydim and clethodim,
- (B4') [foliar-acting herbicides which are effective selectively in soybeans against monocotyledonous harmful plants, selected from the group consisting of] quizalofop-P, [and quizalofop] or
- (B5') nonselective herbicides which can be employed in soybeans for specific purposes, selected from the group consisting of paraquat
- or a mixture of herbicides selected from groups (B1') to [(B4')] (*B5'*) and, optionally, adjuvants or formulation auxiliaries conventionally used in crop protection.

16. A method of controlling harmful plans in soybean crops, comprising applying jointly or separately, pre-emergence, post-emergence or pre- and post-emergence to the plants, parts of the plants, seeds of the plants or the area under cultivation a synergistic effect amount of a herbicidal combination comprising:

(A) a broad-spectrum herbicide from the group of compounds consisting of:
(A1) compounds of the formula (A1), $$H_3C-\underset{\underset{OH}{|}}{\overset{\overset{O}{\|}}{P}}-CH_2-CH_2-\underset{\underset{NH_2}{|}}{CH}-\overset{\overset{O}{\|}}{C}-Z \quad (A1)$$

in which Z is a radical of the formula -OH or a peptide radical of the formula $-NHCH(CH_3)CONHCH(CH_3)COOH$ or $-NHCH(CH_3)CONHCH[CH_2CH(CH_3)_2]COOH$, and their esters and salts and other phosphinothricin derivatives, and (B) one or more herbicides selected from the group consisting of:
- (B1) foliar-acting and/or soil-acting herbicides which are effective selectively in soybeans against monocotyledonous and predominantly dicotyledonous harmful plants, selected from the group consisting of trifluralin, alachlor, ethalfluralin, fluthiamide, vernolate,
- (B2) herbicides which are effective selectively in soybeans against dicotyledonous harmful plants, from the group consisting of chlortoluron, oxyfluorfen, 2,4-DB, [2,4-D,] diclosulam,
- (B3) foliar- and soil-acting herbicides which are effective selectively in soybeans against monocotyledonous harmful plants, from the group consisting of cycloxydim and clethodim,
- (B4) foliar-acting herbicides which are effective selectively in soybeans against monocotyledonous harmful plants, from the group consisting of quizalofop-P, quizalofop, fenoxaprop, fluazifop-P, fluazifop, haloxyfop, and haloxyfop-P or
- (B5) nonselective herbicides which can be employed in soybeans for specific purposes, from the group consisting of paraquat or and optionally at least one safener, whereby the soybean crops are tolerant to the herbicides (A) and (B) which form a constituent of the combination.

*21. A method of controlling harmful plants in soybean crops, comprising applying jointly or separately, pre-emergence, post-emergence or pre- and post-emergence to the plants, parts of the plants, seeds of the plants of the area under cultivation a synergistic effective amount of a herbicidal combination comprising:*

*(A) a broad-spectrum herbicide selected from the group consisting of:*
*(A1) compounds of the formula (A1),*

$$H_3C-\underset{\underset{OH}{|}}{\overset{\overset{O}{\|}}{P}}-CH_2-CH_2-\underset{\underset{NH_2}{|}}{CH}-\overset{\overset{O}{\|}}{C}-Z \quad (A1)$$

*wherein Z is a radical of the formula -OH or a peptide radical of the formula $-NHCH(CH_3)CONHCH(CH_3)COOH$ or*
*$-NHCH(CH_3)CONHCH[CH_2CH(CH_3)_2]COOH$, and their esters and salts and other phosphinothricin derivatives,*

(B) one or more herbicides selected from the group consisting of:
  (B1) foliar-acting and/or soil-acting herbicides which are effective selectively in soybeans against monocotyledonous and predominantly dicotyledonous harmful plants, selected from the group consisting of trifluralin, alachlor, ethalfluralin, fluthiamide and vernolate,
  (B2) foliar-acting and/or soil acting herbicides which are effective selectively in soybeans against dicotyledonous harmful plants, selected from the group consisting of chlortoluron, oxyfluorfen, 2,4-DB, 2,4-D and diclosulam,
  (B3) foliar- and soil-acting herbicides which are effective selectively in soybeans against monocotyledonous harmful plants, selected from the group consisting of cycloxydim and clethodim,
  (B4) foliar-acting herbicides which are effective selectively in soybeans against monocotyledonous harmful plants, selected from the group consisting of quizalofop-P, quizalofop, fluazifop-P, fluazifop, haloxyfop and haloxyfop-P or
  (B5) nonselective herbicides which can be employed in soybeans for specific purposes, selected from the group consisting of paraquat or
  and optionally at least one safener,
  whereby the soybean crops are tolerant to the herbicides (A) and (B) which form a constituent of the combination.

22. The method according to claim 21, wherein the herbicide (B) is selected from the group consisting of:
  (B1) foliar-acting and/or soil-acting herbicides which are effective selectively in soybeans against monocotyledonous and predominantly dicotyledonous harmful plants, selected from the group consisting of trifluralin, alachlor, ethalfluralin, fluthiamide and vernolate,
  (B2) chlortoluron and diclosulam,
  (B3) foliar- and soil-acting herbicides which are effective selectively in soybeans against monocotyledonous harmful plants, selected from the group consisting of cycloxydim and clethodim,
  (B4) foliar-acting herbicides which are effective selectively in soybeans against monocotyledonous harmful plants, selected from the group consisting of quizalofop-P, quizalofop, fluazifop-P, fluazifop, haloxyfop and haloxyfop-P or
  (B5) nonselective herbicides which can be employed in soybeans for specific purposes, selected from the group consisting of paraquat or
  a mixture of herbicides selected from groups (B1) to (B5).

23. The method according to claim 22, wherein the herbicide (A) is glufosinate-ammonium.

24. The method according to claim 21, wherein the herbicidal combination further comprises other crop protection agents.

25. The method according to claim 21, wherein the herbicidal combination further comprises adjuvants and formulation auxiliaries conventionally used in crop protection.

26. A synergistic herbicidal combination, comprising a synergistic effective amount consisting of glufosinate-ammonium and one or more herbicides selected from the group consisting of:
  (B1') foliar-acting and/or soil-acting herbicides which are effective selectively in soybeans against monocotyledonous and predominantly dicotyledonous harmful plants, selected from the group consisting of alachlor;
  (B2') oxyfluorfen;
  (B3') foliar-acting and/or soil acting herbicides herbicides which are effective selectively in soybeans against dicotyledonous harmful plants selected from the group consisting of cycloxydim and clethodim; and
  (B4') foliar-acting herbicides which are effective selectively in soybeans against monocotyledonous harmful plants, selected from the group consisting of quizalofop-P, fluazifop-P and haloxyfop-P;
  or a mixture of herbicides selected from groups (B1') to (B4') and, optionally, adjuvants or formulation auxiliaries conventionally used in crop protection.

27. The synergistic herbicidal combination of claim 26, comprising a synergistic effective amount consisting of glufosinate-ammonium and one or more herbicides selected from the group consisting of:
  (B1') foliar-acting and/or soil-acting herbicides which are effective selectively in soybeans against monocotyledonous and predominantly dicotyledonous harmful plants, selected from the group consisting of alachlor and fluthiamide;
  (B2') oxyfluorfen;
  (B3') foliar-acting and/or soil acting herbicides herbicides which are effective selectively in soybeans against dicotyledonous harmful plants selected from the group consisting of cycloxydim and clethodim;
  (B4') foliar-acting herbicides which are effective selectively in soybeans against monocotyledonous harmful plants, selected from the group consisting of fluazifop-P and haloxyfop-P;
  or a mixture of herbicides selected from groups (B1') to (B4') and, optionally, adjuvants or formulation auxiliaries conventionally used in crop protection.

28. A herbicidal combination as claimed in claim 26 comprising alachlor.

29. A herbicidal combination as claimed in claim 26 comprising cycloxydim.

30. A herbicidal combination as claimed in claim 26 comprising clethodim.

31. A herbicidal combination as claimed in claim 26 comprising quizalofop-P.

32. A herbicidal combination as claimed in claim 26 comprising fluazifop-P.

33. A herbicidal combination as claimed in claim 26 comprising haloxyfop-P.

34. A method for regulating the growth of soybean plants, comprising applying a synergistically effective amount of a synergistic herbicidal combination according to claim 26 to said plants.

35. The method of claim 34, wherein the one or more herbicides selected from the group of:
  (B1') foliar-acting and/or soil-acting herbicides which are effective selectively in soybeans against monocotyledonous and predominantly dicotyledonous harmful plants, selected from the group consisting of trifluralin, alachlor, and fluthiamide;
  (B2') oxyfluorfen;
  (B3') foliar-acting and/or soil acting herbicides herbicides which are effective selectively in soybeans against dicotyledonous harmful plants selected from the group consisting of cycloxydim and clethodim; and
  (B4') foliar-acting herbicides which are effective selectively in soybeans against monocotyledonous harmful plants, selected from the group consisting of quizalofop-P, fluziafop-P-ethyl and haloxyfop-P;
  or a mixture of herbicides selected from groups (B1') to (B4') and, optionally, adjuvants or formulation auxiliaries conventionally used in crop protection.

36. The method according to claim 34, wherein the yield on constituents of soybean plants are influenced.

37. A method of controlling harmful plants in soybean crops, comprising applying jointly or separately, pre-emergence, post-emergence or pre- and post-emergence to the plants, parts of the plants, seeds of the plants or the area under cultivation a synergistic effective amount of a herbicidal combination comprising:

(A) a broad-spectrum herbicide selected from the group consisting of:
(A2) compounds of the formula (A2) and their salts,

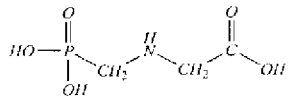

(A2)

and
(B) one or more herbicides selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, alachlor and fluthiamide;
(B2) foliar-acting and/or soil-acting herbicides which are effective selectively in soybeans against dicotyledonous harmful plants, selected from the group consisting of oxyfluorfen, fomesafen, flumiclorac;
(B3) foliar- and soil-acting herbicides which are effective selectively in soybeans against monocotyledonous harmful plants, selected from the group consisting of cycloxydim and clethodim; and
(B4) foliar-acting herbicides which are effective selectively in soybeans against monocotyledonous harmful plants, selected from the group consisting of quizalofop-P, fenoxaprop-P, fenoxaprop, fluazifop-P, fluazifop, haloxyfop, and haloxyfop-P;
and optionally at least one safener,
whereby the soybean crops are tolerant to the herbicides (A) and (B) which form a constituent of the combination.

38. The method according to claim 37, wherein the herbicide (A) is glyphosate-isopropylammonium.

39. The method according to claim 37, wherein the herbicide (B) is selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, alachlor and fluthiamide;
(B2) foliar-acting and/or soil-acting herbicides which are effective selectively in soybeans against dicotyledonous harmful plants, selected from the group consisting of fomesafen and flumiclorac;
(B3) foliar -and soil-acting herbicides which are effective selectively in soybeans against monocotyledonous harmful plants, selected from the group consisting of cycloxydim and clethodim; and
(B4) foliar-acting herbicides which are effective selectively in soybeans against monocotyledonous harmful plants, selected from the group consisting of quizalofop-P, fenoxaprop-P, fenoxaprop, fluazifop-P, fluazifop, haloxyfop, and haloxyfop-P.

40. The method according to claim 39, wherein the herbicide (B) is selected from the group consisting of clomazone, fluthiamide and fomesafen.

41. The method according to claim 37, wherein the herbicidal combination further comprises other crop protection agents.

42. The method according to claim 37, wherein the herbicidal combination further comprises adjuvants and formulation auxiliaries conventionally used in crop protection.

43. The method as claimed in claim 37 comprising trifluralin.

44. The method as claimed in claim 37 comprising clomazone.

45. The method as claimed in claim 37 comprising alachlor.

46. The method as claimed in claim 37 comprising fluthiamide (=flufenacet).

47. The method as claimed in claim 37 comprising oxyfluorfen.

48. The method as claimed in claim 37 comprising lactofen.

49. The method as claimed in claim 37 comprising fomesafen.

50. The method as claimed in claim 37 comprising flumiclorac.

51. The method as claimed in claim 37 comprising cycloxydim.

52. The method as claimed in claim 37 comprising clethodim.

53. The method as claimed in claim 37 comprising quizalofop-P.

54. The method as claimed in claim 37 comprising fenoxaprop-P.

55. The method as claimed in claim 37 comprising fluazifop-P.

56. The method as claimed in claim 37 comprising haloxyfop-P.

57. A synergistic herbicidal combination, comprising a synergistic effective amount consisting of glyphosate-isopropylammonium and one or more herbicides selected from the group consisting of:

(B1') foliar-acting and/or soil-acting herbicides which are effective selectively in soybeans against monocotyledonous and predominantly dicotyledonous harmful plants, selected from the group consisting of alachlor;

(B2') herbicides which are effective selectively in soybeans against dicotyledonous harmful plants, from the group consisting of oxyfluorfen and flumiclorac;

(B3') foliar- and soil-acting herbicides which are effective selectively in soybeans against monocotyledonous harmful plants, selected from the group consisting of cycloxydim and clethodim; and (B4') quizalofop-P.

58. A method for regulating the growth of soybean plants, comprising applying a synergistically effective amount of a synergistic herbicidal combination according to claim 57 to said plants.

59. The method according to claim 58, wherein the yield on constituents of soybean plants are influenced.

60. A method of controlling harmful plants in soybean crops, comprising applying post-emergence to the plants, parts of the plants, or the area under cultivation a synergistic effective amount of a herbicidal combination comprising:

(A) a broad-spectrum herbicide selected from the group consisting of:
(A2) compounds of the formula (A2) and their salts,

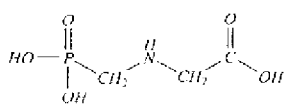

and
(B) one or more herbicides selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, flumetsulam, alachlor, sulfentrazone, ethalfluralin, fluthiamide, vernolate and flumioxazin,
(B2) herbicides which are effective selectively in soybeans against dicotyledonous harmful plants, selected from the group consisting of chlortoluron, oxyfluorfen, lactofen, fomesafen, flumiclorac, 2,4-DB, 2,4-D, diclosulam, and cloransulam,
(B3) foliar- and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, haloxyfop-P or
(B5) nonselective herbicides which can be employed in soybeans for specific purposes, selected from the group consisting of paraquat or
and optionally at least one safener,
whereby the soybean crops are tolerant to the herbicides (A) and (B) which form a constituent of the combination.

61. The method of claim 60, wherein
(B) one or more herbicides is selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, flumetsulam, alachlor and fluthiamide,
(B2) foliar-acting and/or soil-acting herbicides which are effective selectively in soybeans against dicotyledonous harmful plants, selected from the group consisting of oxyfluorfen, lactofen, fomesafen, flumiclorac and cloransulam;
(B3) foliar- and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, and haloxyfop-P;
and optionally at least one safener,
whereby the soybean crops are tolerant to the herbicides (A) and (B) which form a constituent of the combination.

62. The method according to claim 61, wherein the herbicide (A) is glyphosate-isopropylammonium.
63. The method according to claim 62, wherein the herbicide (B) is selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, alachlor and fluthiamide,
(B2) foliar-acting and/or soil-acting herbicides which are effective selectively in soybeans against dicotyledonous harmful plants, selected from the group consisting of fomesafen, flumiclorac and cloransulam;
(B3) foliar- and soil-acting herbicides which are effective selectively in soybeans against monocotyledonous harmful plants, selected from the group consisting of sethoxydim, cycloxydim and clethodim; and
(B4) foliar-acting herbicides which are effective selectively in soybeans against monocotyledonous harmful plants, selected from the group consisting of quizalofop-P, quizalofop, fenoxprop-P, fenoxaprop, fluazifop-P, fluazifop, haloxyfop, and haloxyfop-P.

64. The method according to claim 63, wherein the herbicide (B) is selected from the group consisting of clomazone, fluthiamide, fomensafen and quizalofop-P.

65. A method of controlling harmful plants in soybean crops, comprising applying post-emergence to the plants, parts of the plants, seeds of the plants or the area under cultivation a synergistic effective amount of a herbicidal combination comprising:
(A) a broad-spectrum herbicide selected from the group consisting of:
(A2) compounds of the formula (A2) and their salts,

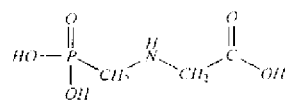

and
(B) one or more herbicides selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, flumetsulam, alachlor, sulfentrazone, ethalfluralin, fluthiamide, vernolate and flumioxazin.
(B2) herbicides which are effective selectively in soybeans against dicotyledonous harmful plants, selected from the group consisting of chlortoluron, oxyfluorfen, lactofen, fomesafen, flumiclorac, 2,4-DB, 2,4-D, diclosulam and cloransulam,
(B3) foliar- and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, and haloxyfop-P; or
(B5) nonselective herbicides which can be employed in soybeans for specific purposes, selected from the group consisting of paraquat;

and optionally at least one safener, whereby the soybean crops are tolerant to the herbicides (A) and (B) which form a constituent of the combination,
wherein the ratio of (A) to (B) by weight is from 2000:1 to 1:2000.

66. The method as claimed in claim 65 wherein the ratio of (A) to (B) by weight is from 2000:1 to 1:1000.

67. The method as claimed in claim 65 wherein the ratio of (A) to (B) by weight is from 200:1 to 1:200.

68. The method as claimed in claim 65 wherein (B1) is trifluralin and the ratio of (A2) to (B1) by weight is from 200:1 to 1:50.

69. The method as claimed in claim 65 wherein (B1) is clomazone and the ratio of (A2) to (B1) by weight is from 200:1 to 1:50.

70. The method as claimed in claim 65 wherein (B1) is flumetsulam and the ratio of (A2) to (B1) by weight is from 200:1 to 1:50.

71. The method as claimed in claim 65 wherein (B1) is alachlor and the ratio of (A2) to (B1) by weight is from 200:1 to 1:50.

72. The method as claimed in claim 65 wherein (B1) is sulfentrazone and the ratio of (A2) to (B1) by weight is from 200:1 to 1:50.

73. The method as claimed in claim 65 wherein (B1) is ethalfluralin and the ratio of (A2) to (B1) by weight is from 200:1 to 1:50.

74. The method as claimed in claim 65 wherein (B1) is fluthiamide and the ratio of (A2) to (B1) by weight is from 200:1 to 1:50.

75. The method as claimed in claim 65 wherein (B1) is vernolate and the ratio of (A2) to (B1) by weight is from 200:1 to 1:50.

76. The method as claimed in claim 65 wherein (B1) is flumioxazin and the ratio of (A2) to (B1) by weight is from 200:1 to 1:50.

77. The method as claimed in claim 65 wherein (B2) is chlortoluron and the ratio of (A2) to (B2) by weight is from 300:1 to 1:200.

78. The method as claimed in claim 65 wherein (B2) is oxyfluorfen and the ratio of (A2) to (B2) by weight is from 300:1 to 1:200.

79. The method as claimed in claim 65 wherein (B2) is lactofen and the ratio of (A2) to (B2) by weight is from 300:1 to 1:200.

80. The method as claimed in claim 65 wherein (B2) is fomesafen and the ratio of (A2) to (B2) by weight is from 300:1 to 1:200.

81. The method as claimed in claim 65 wherein (B2) is flumiclorac and the ratio of (A2) to (B2) by weight is from 300:1 to 1:200.

82. The method as claimed in claim 65 wherein (B2) is 2,4-DB and the ratio of (A2) to (B2) by weight is from 300:1 to 1:200.

83. The method as claimed in claim 65 wherein (B2) is 2,4-D and the ratio of (A2) to (B2) by weight is from 300:1 to 1:200.

84. The method as claimed in claim 65 wherein (B2) is diclosulam and the ratio of (A2) to (B2) by weight is from 300:1 to 1:200.

85. The method as claimed in claim 65 wherein (B2) is cloransulam and the ratio of (A2) to (B2) by weight is from 300:1 to 1:200.

86. The method as claimed in claim 65 wherein (B2) is sethoxydim and the ratio of (A2) to (B2) by weight is from 200:1 to 1:100.

87. The method as claimed in claim 65 wherein (B2) is cycloxydim and the ratio of (A2) to (B2) by weight is from 200:1 to 1:100.

88. The method as claimed in claim 65 wherein (B2) is clethodim and the ratio of (A2) to (B2) by weight is from 200:1 to 1:100.

89. The method as claimed in claim 65 wherein (B2) is quizalofop-P and the ratio of (A2) to (B2) by weight is from 100:1 to 1:10.

90. The method as claimed in claim 65 wherein (B2) is quizalofop and the ratio of (A2) to (B2) by weight is from 100:1 to 1:10.

91. The method as claimed in claim 65 wherein (B2) is fenoxaprop-P and the ratio of (A2) to (B2) by weight is from 100:1 to 1:10.

92. The method as claimed in claim 65 wherein (B2) is fenoxaprop and the ratio of (A2) to (B2) by weight is from 100:1 to 1:10.

93. The method as claimed in claim 65 wherein (B2) is fluazifop-P and the ratio of (A2) to (B2) by weight is from 100:1 to 1:10.

94. The method as claimed in claim 65 wherein (B2) is fluazifop and the ratio of (A2) to (B2) by weight is from 100:1 to 1:10.

95. The method as claimed in claim 65 wherein (B2) is haloxyfop-P and the ratio of (A2) to (B2) by weight is from 100:1 to 1:10.

96. The method as claimed in claim 65 wherein (B2) is haloxyfop and the ratio of (A2) to (B2) by weight is from 100:1 to 1:10.

97. The method of controlling harmful plants in soybean crops, comprising applying post-emergence to the plants, parts of the plants, or the area under cultivation a synergistic effective amount of a herbicidal combination comprising:
(A) a broad-spectrum herbicide selected from the group consisting of:
(A1) compounds of the formula (A1)

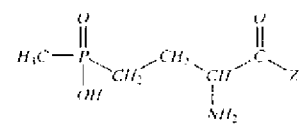

wherein Z is a radical of the formula -OH or a peptide radical of the formula -NHCH(CH$_3$)CONHCH(CH$_3$)COOH or
-NHCH(CH$_3$)CONHCH[CH$_2$CH(CH$_3$)$_2$]COOH, and their esters and salts and other phosphinothricin derivatives,
(B) one or more herbicides selected from the group consisting of:
(B1) foliar-acting and/or soil-acting herbicides which are effective selectively in soybeans against monocotyledonous and predominantly dicotyledonous harmful plants, selected from the group consisting of trifluralin, alachlor, ethalfluralin, fluthiamide, and vernolate,
(B2) herbicides which are effective selectively in soybeans against dicotyledonous harmful plants, selected from the group consisting of chlortoluron, oxyfluorfen, 2,4-DB, 2,4-D, and diclosulam,
(B3) foliar- and soil-acting herbicides which are effective selectively in soybeans against monocotyledonous harmful plants, selected from the group consisting of cycloxydim and clethodim,
(B4) foliar-acting herbicides which are effective selectively in soybeans against monocotyledonous harmful plants, selected from the group consisting of quizalofop-P, quizalofop, fenoxaprop, fluazifop-P, fluazifop, haloxyfop, and haloxyfop-P; or (B5) nonselective herbicides which can be employed in soybeans for specific purposes, selected from the group consisting of paraquat or and optionally at least one safener.

98. A method of controlling harmful plants in soybean crops, comprising applying post-emergence to the plants, parts of the plants, or the area under cultivation a synergistic effective amount of a herbicidal combination comprising:

(A) a broad-spectrum herbicide selected from the group consisting of:
(A3) imidazolinones and their salts; and (B) one or more herbicides selected from the group consisting of:
(B1) foliar-acting and/or soil-acting herbicides which are effective selectively in soybeans against monocotyledonous and predominantly dicotyledonous harmful plants, selected from the group consisting of metribuzin, flumetsulam, alachlor, ethalfluralin, fluthiamide, norflurazone, vernolate, and flumioxazin,
(B2) herbicides which are effective selectively in soybeans against dicotyledonous harmful plants, selected from the group consisting of chlortoluron, oxyfluorfen, fomesafen, 2,4-DB, chlorimuron, diclosulam, fluthiacet, cloransulam, and oxasulfuron,
(B3) foliar- and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop, fluazifop-P, fluazifop, haloxyfop, haloxyfop-P, and propaquizafop or
(B5) nonselective herbicides which can be employed in soybeans for specific purposes, selected from the group consisting of paraquat or
and optionally at least one safener.

99. A method of controlling harmful plants in soybean crops, comprising applying post-emergence to the plants, parts of the plants, or the area under cultivation a synergistic effective amount of a herbicidal combination comprising:

(A) a broad-spectrum herbicide selected from the group consisting of:
(A4) one or more herbicides selected from the group consisting of herbicidal azoles from the protopothyrinogen-oxidase inhibitors (PPO inhibitors); and (B) one or more herbicides selected from the group consisting of:
(B1) foliar-acting and/or soil-acting herbicides which are effective selectively in soybeans against monocotyledonous and predominantly dicotyledonous harmful plants, selected from the group consisting of trifluralin, metribuzin, clomazone, pendimethalin, metolachlor, flumetsulam, dimethenamid, alachlor, linuron, sulfentrazone, ethalfluralin, fluthiamide, norflurazone, vernolate and flumioxazin,
(B2) herbicides which are effective selectively in soybeans against dicotyledonous harmful plants, selected from the group consisting of chlortoluron, bentazone, thifensulfuron, oxyfluorfen, lactofen, fomesafen, flumiclorac, acifluorfen, 2,4-DB, 2,4-D, chlorimuron, diclosulam, fluthiacet, cloransulam and oxasulfuron,
(B3) foliar- and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, haloxyfop-P and propaquizafop or
(B5) nonselective herbicides which can be employed in soybeans for specific purposes, selected from the group consisting of paraquat or
and optionally at least one safener.

100. A method of controlling harmful plants in soybean crops, comprising applying jointly or separately, post-sowing pre-emergence, post-emergence, or pre- and post-emergence to the plants, parts of the plants, seeds of the plants, or the area under cultivation a synergistic effective amount of a herbicidal combination comprising:

compounds of the formula (A2) and their salts,

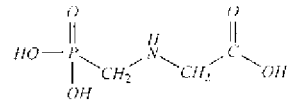

; and (B) is 2,4-D.

101. The method according to claim 100, wherein the herbicide (A) is glyphosate-isopropylammonium.

* * * * *

(12) EX PARTE REEXAMINATION CERTIFICATE (9160th)
United States Patent
Hacker et al.

(10) Number: US 7,105,470 C1
(45) Certificate Issued: Jul. 31, 2012

(54) HERBICIDAL COMPOSITIONS FOR TOLERANT OR RESISTANT SOYBEAN CROPS

(75) Inventors: Erwin Hacker, Hochheim (DE); Hermann Bieringer, Eppstein (DE); Lothar Willms, Hofheim (DE)

(73) Assignee: Bayer Cropscience AG, Monheim (DE)

Reexamination Request:
No. 90/009,711, Mar. 26, 2010

Reexamination Certificate for:
Patent No.: 7,105,470
Issued: Sep. 12, 2006
Appl. No.: 09/371,612
Filed: Aug. 10, 1999

(51) Int. Cl.
*A01N 57/02* (2006.01)
*A01N 43/42* (2006.01)
*A01N 43/52* (2006.01)
*A01N 57/20* (2006.01)
*A01P 13/00* (2006.01)

(52) U.S. Cl. .................. 504/127; 504/128; 504/139; 504/145; 504/132; 504/130

(58) Field of Classification Search .................. None
See application file for complete search history.

(56) References Cited

To view the complete listing of prior art documents cited during the proceeding for Reexamination Control Number 90/009,711, please refer to the USPTO's public Patent Application Information Retrieval (PAIR) system under the Display References tab.

*Primary Examiner* — Bruce Campell

(57) ABSTRACT

Herbicide combinations (A)+(B), if appropriate in the presence of safeners, with an effective content of (A) broad-spectrum herbicides from the group (A1) glufosinate (salts) and related compounds (A2) glyphosate (salts) and related compounds such as sulfosate, (A3) imidazolinones such as imazethapyr, imazapyr, imazaquin, imazamox or their salts and (A4) herbicidal azoles from the group of the protoporphyrinogen oxidase inhibitors (PPO inhibitors) and (B) one or more herbicides from the group of the compounds consisting of (B0) one or more structurally different herbicides from the above-mentioned group (A) and/or (B1) foliar- and/or soil-acting herbicides (residual action) which are effective selectively in soybeans against monocotyladonous and predominantly dicotyledonous harmful plants or (B2) herbicides which are effective selectively in soybeans against dicotyledonous harmful plants, or (B3) foliar- and soil-acting herbicides which are effective selectively in soybeans against monocotyledonous harmful plants or (B4) foliar-acting herbicides which are effective selectively in soybeans against monocotyledonous and dicotyledonous harmful plants or (B5) nonselective herbicides which can be employed in soybeans for specific purposes, such as paraquat (salts), or herbicides from several of groups (B0) to (B5)

are suitable for controlling harmful plants in soybeans which consists of tolerant or resistant mutants or transgenic soybean plants and the soybean crops are tolerant to the herbicides (A) and (B), if appropriate in the presence of safeners, which are contained in the combination.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13-15 is confirmed.

Claims 1-4, 10 and 16 are determined to be patentable as amended.

Claims 5, 6, 11, 12, 17-20, dependent on an amended claim, are determined to be patentable.

New claims 21-101 are added and determined to be patentable.

Claims 7-9 were not reexamined.

1. A method of controlling harmful plants in soybean crops, comprising applying jointly or separately, pre-emergence, post-emergence or pre- and post- emergence to the plants, parts of the plants, seeds of the plants or the area under cultivation a synergistic effective amount of a herbicidal combination comprising:
   (A) a broad-spectrum herbicide selected from the group consisting of:
   (A1) compounds of the formula (A1),

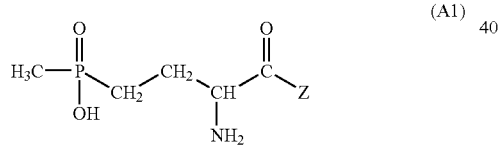

wherein Z is a radical of the formula -OH or a peptide radical of the formula –NHCH(CH₃)CONHCH(CH₃)COOH or –NHCH(CH₃)CONHCH[CH₂CH(CH₃)₂]COOH, and their esters and salts and other phosphinothricin derivatives,
   (A2) compounds of the formula (A2) and their salts,

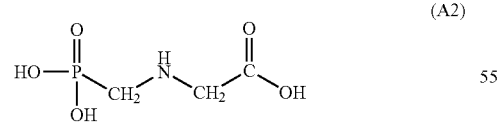

(A3) imidazolinones and their salts and
   (A4) herbicidal azoles from the protoporphyrinogen-oxidase inhibitors (PPO inhibitors) and
(B) one or more herbicides selected from the group consisting of:
   (B1) foliar-acting and/or soil-acting herbicides which are effective selectively in soybeans against monocotyledonous and predominantly dicotyledonous harmful plants, selected from the group consisting of trifluralin, metribuzin, clomazone, pendimethalin, metolachlor, flumetsulam, dimethenamid, alachlor, linuron, sulfentrazone, ethalfluralin, fluthiamide, norflurazone, vernolate and flumioxazin,
   (B2) herbicides which are effective selectively in soybeans against dicotyledonous harmful plants, selected from the group consisting of chlortoluron, bentazone, thifensulfuron, oxyfluorfen, lactofen, fomesafen, flumiclorac, acifluorfen, 2,4-DB, 2,4-D, chlorimuron, diclosulam, fluthiacet, cloransulam and oxasulfuron,
   (B3) foliar- and soil-acting herbicides which are effective selectively in soybeans against monocotyledonous harmful plants, selected from the group consisting of sethoxydim, cycloxydim and clethodim,
   (B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop-P and propaquizafop or
   (B5) nonselective herbicides which can be employed in soybeans for specific purposes, selected from the group consisting of paraquat or
and optionally at least one safener,
whereby the soybean crops are tolerant to the herbicides (A) and (B) which form a constitutent of the combination, with the exception of the following combinations:
   a) combinations comprising compounds of group (A1) and compounds of group (B) selected from the group consisting of cloransulam, metolachlor, metribuzin, chlorimuron, dimethenamid, pendimethalin, bentazone, clomazone, thifensulfuron, flumiclorac, flumetsulam, linuron, sethoxydim, acifluorfen, fomesafen, sulfentrazone, flumioxazin, lactofen, norflurazone, propaquizafop, fenoxaprop-P, fluthiacet and oxasulfuron;
   b) combinations comprising compounds of group (A2) and compounds of group (B) selected from the group consisting of metolachlor, dimethenamid, metribuzin, chlorimuron, pendimethalin, *flumetsulam, sulfentrazone, thifensulfuron, lactofen,* bentazone, linuron, norflurazone, propaquizafop, acifluorfen, fluthiacet, *cloransulam, sethoxydim, quizalofop* and oxasulfuron;
   c) combinations comprising compounds of group (A3) from the group consisting of imazethapyr, and compounds of group (B) from the group consisting of 2,4-D, metolachlor, bentazone, clomazone, thifensulfuron, flumiclorac, pendimethalin, trifluralin, sulfentrazone, lactofen, dimethenamid, acifluorfen and fenoxaprop-P;
   d) combinations comprising compounds of group (A3) selected from the group consisting of 2,4-D, imazaquin, and compounds of group (B) selected from the group consisting of pendimethalin, trifluralin and metolachlor;
   e) combinations comprising compounds of group (A3) selected from the group consisting of imazamox (AC299263), and compounds of group (B) selected from the group consisting of bentazone and trifluralin;
   f) combinations comprising compounds of group (A3) selected from the group consisting of imazapyr, and compounds of group (B) selected from the group consisting of metolachlor.

4. The method according to claim 1, wherein the herbicide (B) is selected from the group consisting of:
- (B1) foliar-acting and/or soil-acting herbicides which are effective selectively in soybeans against monocotyledonous and predominantly dicotyledonous harmful plants, selected from the group consisting of trifluralin, flumetsulam, alachlor, ethalfluralin, fluthiamide and vernolate, [(B2) chlortolurondiclosulam,]
- *(B2) chlortoluron and diclosulam;*
- (B3) foliar- and soil-acting herbicides which are effective selectively in soybeans against monocotyledonous harmful plants, selected from the group consisting of cycloxydim and clethodim,
- (B4) foliar-acting herbicides which are effective selectively in soybeans against monocotyledonous harmful plants, selected from the group consisting of quizalofop-P, quizalofop, fluazifop-P, fluazifop, haloxyfop and haloxyfop-P or
- (B5) nonselective herbicides which can be employed in soybeans for specific purposes, selected from the group consisting of paraquat or
- [a mixture of herbicides selected from groups (B0) to (B4)] *a mixture of herbicides selected from the groups consisting of (B1) to (B5).*

10. A synergistic herbicidal combination, comprising a synergistic effective amount consisting of glyphosate-ammonium and one or more herbicides selected from the group consisting of:
- (B1') foliar-acting and/or soil-acting herbicides which are effective selectively in soybeans against monocotyledonous and predominantly dicotyledonous harmful plants, selected from the group consisting of [flumetsulam, alachlor, ethalfluralin, vernolate and flumioxazin] *alachlor, ethalfluralin, vernolate and flumioxazin*,
- (B2') herbicides which are effective selectively in soybeans against dicotyledonous harmful plants, from the group consisting of chlortoluron, oxyfluorfen, [lactofen,] fomesafen, flumiclorac and diclosulam,
- (B3') foliar- and soil-acting herbicides which are effective selectively in soybeans against monocotyledonous harmful plants, selected from the group consisting of [sethoxydim,] cycloxydim and clethodim,
- (B4') [foliar-acting herbicides which are effective selectively in soybeans against monocotyledonous harmful plants, selected from the group consisting of] quizalofop-P[, and quizalofop] or
- (B5') nonselective herbicides which can be employed in soybeans for specific purposes, selected from the group consisting of paraquat
- or a mixture of herbicides selected from groups (B1') to [(B4')] *(B5')* and, optionally, adjuvants or formulation auxiliaries conventionally used in crop protection.

16. A method of controlling harmful plans in soybean crops, comprising applying jointly or separately, pre-emergence, post-emergence or pre- and post-emergence to the plants, parts of the plants, seeds of the plants or the area under cultivation a synergistic effect amount of a herbicidal combination comprising:

(A) a broad-spectrum herbicide from the group of the compound consisting of:
(A1) compounds of the formula (A1),

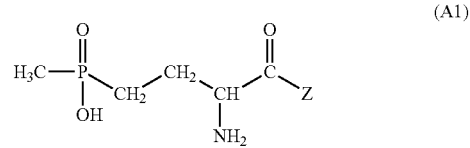

in which Z is a radical of the formula -OH or a peptide radical of the formula– $NHCH(CH_3)CONHCH(CH_3)COOH$ or $-NHCH(CH_3)CONHCH[CH_2CH(CH_3)_2]COOH$, and their esters and salts and other phosphinothricin derivatives, and (B) one or more herbicides selected from the group consisting of:
- (B1) foliar-acting and/or soil-acting herbicides which are effective selectively in soybeans against monocotyledonous and predominantly dicotyledonous harmful plants, selected from the group consisting of trifluralin, alachlor, ethalfluralin, fluthiamide, vernolate,
- (B2) herbicides which are effective selectively in soybeans against dicotyledonous harmful plants, from the group consisting of chlortoluron, oxyfluorfen, 2,4-DB, [2,4-D,] diclosulam,
- (B3) foliar- and soil-acting herbicides which are effective selectively in soybeans against monocotyledonous harmful plants, from the group consisting of cycloxydim and clethodim,
- (B4) foliar-acting herbicides which are effective selectively in soybeans against monocotyledonous harmful plants, from the group consisting of quizalofop-P, quizalofop, fenoxaprop, fluazifop-P, fluazifop, haloxyfop and haloxyfop-P or
- (B5) nonselective herbicides which can be employed in soybeans for specific purposes, from the group consisting of paraquat or and optionally at least one safener, whereby the soybean crops are tolerant to the herbicides (A) and (B) which form a constituent of the combination.

*21. A method of controlling harmful plants in soybean crops, comprising applying jointly or separately, pre-emergence, post-emergence or pre- and post-emergence to the plants, parts of the plants, seeds of the plants of the area under cultivation a synergistic effective amount of a herbicidal combination comprising:*

*(A) a broad-spectrum herbicide selected from the group consisting of:*
*(A1) compounds of the formula (A1),*

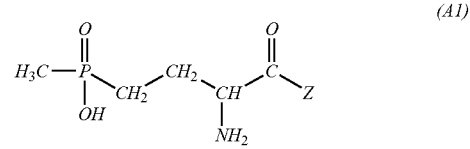

*wherein Z is a radical of the formula -OH or a peptide radical of the formula $-NHCH(CH_3)CONHCH(CH_3)COOH$ or*

*$-NHCH(CH_3)CONHCH[CH_2CH(CH_3)_2]COOH$, and their esters and salts and other phosphinothricin derivatives,*

(B) one or more herbicides selected from the group consisting of:
- (B1) foliar-acting and/or soil-acting herbicides which are effective selectively in soybeans against monocotyledonous and predominantly dicotyledonous harmful plants, selected from the group consisting of trifluralin, alachlor, ethalfluralin, fluthiamide and vernolate,
- (B2) foliar-acting and/or soil acting herbicides which are effective selectively in soybeans against dicotyledonous harmful plants, selected from the group consisting of chlortoluron, oxyfluorfen, 2,4-DB, 2,4-D and diclosulam,
- (B3) foliar- and soil-acting herbicides which are effective selectively in soybeans against monocotyledonous harmful plants, selected from the group consisting of cycloxydim and clethodim,
- (B4) foliar-acting herbicides which are effective selectively in soybeans against monocotyledonous harmful plants, selected from the group consisting of quizalofop-P, quizalofop, fluazifop-P, fluazifop, haloxyfop and haloxyfop-P or
- (B5) nonselective herbicides which can be employed in soybeans for specific purposes, selected from the group consisting of paraquat or and optionally at least one safener, whereby the soybean crops are tolerant to the herbicides (A) and (B) which form a constituent of the combination.

22. The method according to claim 21, wherein the herbicide (B) is selected from the group consisting of:
- (B1) foliar-acting and/or soil-acting herbicides which are effective selectively in soybeans against monocotyledonous and predominantly dicotyledonous harmful plants, selected from the group consisting of trifluralin, alachlor, ethalfluralin, fluthiamide and vernolate,
- (B2) chlortoluron and diclosulam,
- (B3) foliar- and soil-acting herbicides which are effective selectively in soybeans against monocotyledonous harmful plants, selected from the group consisting of cycloxydim and clethodim,
- (B4) foliar-acting herbicides which are effective selectively in soybeans against monocotyledonous harmful plants, selected from the group consisting of quizalofop-P, quizalofop, fluazifop-P, fluazifop, haloxyfop and haloxyfop-P or
- (B5) nonselective herbicides which can be employed in soybeans for specific purposes selected from the group consisting of paraquat or a mixture of herbicides selected from groups (B1) to (B5).

23. The method according to claim 22, wherein the herbicide (A) is glufosinate-ammonium.

24. The method according to claim 21, wherein the herbicidal combination further comprises other crop protection agents.

25. The method according to claim 21, wherein the herbicidal combination further comprises adjuvants and formulation auxiliaries conventionally used in crop protection.

26. A synergistic herbicidal combination, comprising a synergistic effective amount consisting of glufosinate-ammonium and one or more herbicides selected from the group consisting of:
- (B1') foliar-acting and/or soil-acting herbicides which are effective selectively in soybeans against monocotyledonous and predominantly dicotyledonous harmful plants, selected from the group consisting of trifluralin, alachlor, and fluthiamide;
- (B2') oxyfluorfen:
- (B3') foliar-acting and/or soil acting herbicides herbicides which are effective selectively in soybeans against dicotyledonous harmful plants selected from the group consisting of cycloxydim and clethodim; and
- (B4') foliar-acting herbicides which are effective selectively in soybeans against monocotyledonous harmful plants, selected from the group consisting of quizalofop-P, fluazifop-P and haloxyfop-P;

or a mixture of herbicides selected from groups (B1') to (B4') and, optionally, adjuvants or formulation auxiliaries conventionally used in crop protection.

27. The synergistic herbicidal combination of claim 26, comprising a synergistic effective amount consisting of glufosinate-ammonium and one or more herbicides selected from the group consisting of:
- (B1') foliar-acting and/or soil-acting herbicides which are effective selectively in soybeans against monocotyledonous and predominantly dicotyledonous harmful plants, selected from the group consisting of alachlor and fluthiamide;
- (B2') oxyfluorfen;
- (B3') foliar-acting and/or soil acting herbicides herbicides which are effective selectively in soybeans against dicotyledonous harmful plants selected from the group consisting of cycloxydim and clethodim;
- (B4') foliar-acting herbicides which are effective selectively in soybeans against monocotyledonous harmful plants, selected from the group consisting of fluazifop-P and haloxyfop-P;

or a mixture of harbicides selected from groups (B1') to (B4') and, optionally, adjuvants or formulation auxiliaries conventionally used in crop protection.

28. A herbicidal combination as claimed in claim 26 comprising trifluralin.

29. A herbicidal combination as claimed in claim 26 comprising alachlor.

30. A herbicidal combination as claimed in claim 26 comprising fluthiamide.

31. A herbicidal combination as claimed in claim 26 comprising oxyfluorfen.

32. A herbicidal combination as claimed in claim 26 comprising cycloxydim.

33. A herbicidal combination as claimed in claim 26 comprising clethodim.

34. A herbicidal combination as claimed in claim 26 comprising quizalofop-P.

35. A herbicidal combination as claimed in claim 26 comprising fluazifop-P.

36. A herbicidal combination as claimed in claim 26 comprising haloxyfop-P.

37. A method for regulating the growth of soybean plants, comprising applying a synergistically effective amount of a synergistic herbicidal combination according to claim 26 to said plants.

38. The method of claim 37, wherein the one or more herbicides selected from the group consisting of:
- (B1') foliar-acting and/or soil-acting herbicides which are effective selectively in soybeans against monocotyledonous and predominantly dicotyledonous harmful plants, selected from the group consisting of trifluralin, alachlor, and fluthiamide;
- (B2') oxyfluorfen;
- (B3') foliar-acting and/or soil acting herbicides herbicides which are effective selectively in soybeans against dicotyledonous harmful plants selected from the group consisting of cycloxydim and clethodim; and (B4') foliar-acting herbicides which are effective selectively in soybeans against monocotyledonous harmful plants, selected from the group consisting of quizalofop-P, fluziafop-P-ethyl and haloxyfop-P;

or a mixture of herbicides selected from groups (B1') to (B4') and, optionally, adjuvants or formulation auxiliaries conventionally used in crop protection.

39. The method according to claim 37, wherein the yield on constitutents of soybean plants are influenced.

40. A method of controlling harmful plants in soybean crops, comprising applying jointly or separately, pre-emergence, post-emergence or pre- and post-emergence to the plants, parts of the plants, seeds of the plants or the area under cultivation a synergistic effective amount of a herbicidal combination comprising:

(A) a broad-spectrum herbicide selected from the group consisting of:

(A2) compounds of the formula (A2) and their salts,

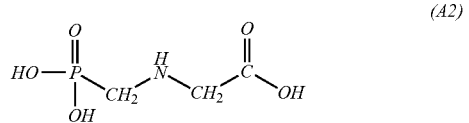

(A2)

and (B) one or more herbicides selected from the group consisting of:

(B1) foliar-acting and/or soil-acting herbicides which are effective selectively in soybeans against monocotyledonous and predominantly dicotyledonous harmful plants, selected from the group consisting of trifluralin, clomazone, alachlor and fluthiamide;

(B2) foliar-acting and/or soil-acting herbicides which are effective selectively in soybeans against dicotyledonous harmful plants, selected from the group consisting of oxyfluorfen, fomesafen, flumiclorac;

(B3) foliar- and soil-acting herbicides which are effective selectively in soybeans against monocotyledonous harmful plants, selected from the group consisting of cycloxydim and clethodim; and (B4) foliar-acting herbicides which are effective selectively in soybeans against monocotyledonous harmful plants, selected from the group consisting of quizalofop-P, fenoxaprop-P, fenoxaprop, fluazifop-P, fluazifop, haloxyfop, and haloxyfop-P;

and optionally at least one safener, whereby the soybean crops are tolerant to the herbicides (A) and (B) which form a constituent of the combination.

41. The method according to claim 40, wherein the herbicide (A) is glyphosate-isopropylammonium.

42. The method according to claim 40, wherein the herbicide (B) is selected from the group consisting of:

(B1) foliar-acting and/or soil-acting herbicides which are effective selectively in soybeans against monocotyledonous and predominantly dicotyledonous harmful plants, selected from the group consisting of trifluralin, clomazone, alachlor and fluthiamide;

(B2) foliar-acting and/or soil-acting herbicides which are effective selectively in soybeans against dicotyledonous harmful plants, selected from the group consisting of fomesafen and flumiclorac;

(B3) foliar -and soil-acting herbicides which are effective selectively in soybeans against monocotyledonous harmful plants, selected from the group consisting of cycloxydim and clethodim; and (B4) foliar-acting herbicides which are effective selectively in soybeans against monocotyledonous harmful plants, selected from the group consisting of quizalofop-P, fenoxaprop-P, fenoxaprop, fluazifop-P, fluazifop, haloxyfop, and haloxyfop-P.

43. The method according to claim 42, wherein the herbicide (B) is selected from the group consisting of clomazone, fluthiamide and fomensafen.

44. The method according to claim 40, wherein the herbicidal combination further comprises other crop protection agents.

45. The method according to claim 40, wherein the herbicidal combination further comprises adjuvants and formulation auxiliaries conventionally used in crop protection.

46. The method as claimed in claim 40 comprising trifluralin.

47. The method as claimed in claim 40 comprising clomazone.

48. The method as claimed in claim 40 comprising alachlor.

49. The method as claimed in claim 40 comprising fluthiamide (=flufenacet).

50. The method as claimed in claim 40 comprising oxyfluorfen.

51. The method as claimed in claim 40 comprising lactofen.

52. The method as claimed in claim 40 comprising fomesafen.

53. The method as claimed in claim 40 comprising flumiclorac.

54. The method as claimed in claim 40 comprising cycloxydim.

55. The method as claimed in claim 40 comprising clethodim.

56. The method as claimed in claim 40 comprising quizalofop-P.

57. The method as claimed in claim 40 comprising fenoxaprop-P.

58. The method as claimed in claim 40 comprising fluazifop-P.

59. The method as claimed in claim 40 comprising haloxyfop-P.

60. A synergistic herbicidal combination, comprising a synergistic effective amount consisting of glyphosate-ammonium and one or more herbicides selected from the group consisting of:

(B1') foliar-acting and/or soil-acting herbicides which are effective selectively in soybeans against monocotyledonous and predominantly dicotyledonous harmful plants, selected from the group consisting of alachlor;

(B2') herbicides which are effective selectively in soybeans against dicotyledonous harmful plants, from the group consisting of oxyfluorfen, fomesafen, flumiclorac;

(B3') foliar- and soil-acting herbicides which are effective selectively in soybeans against monocotyledonous harmful plants, selected from the group consisting of cycloxydim and clethodim; and (B4') quizalofop-P.

61. A method for regulating the growth of soybean plants, comprising applying a synergistically effective amount of a synergistic herbicidal combination according to claim 60 to said plants.

62. The method according to claim 61, wherein the yield on constitutents of soybean plants are influenced.

63. A method of controlling harmful plants in soybean crops, comprising applying post-emergence to the plants, parts of the plants, or the area under cultivation a synergistic effective amount of a herbicidal combination comprising:
(A) a broad-spectrum herbicide selected from the group consisting of:
(A2) compounds of the formula (A2) and their salts,

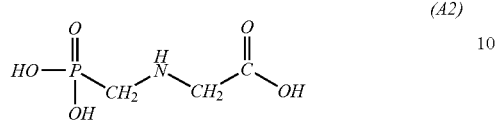

(A2)

and
(B) one or more herbicides selected from the group consisting of:
(B1) foliar-acting and/or soil-acting herbicides which are effective selectively in soybeans against monocotyledonous and predominantly dicotyledonous harmful plants, selected from the group consisting of trifluralin, metribuzin, clomazone, pendimethalin, metolachlor, flumetsulam, dimethenamid, alachlor, linuron, sulfentrazone, ethalfluralin, fluthiamide, norflurazone, vernolate and flumioxazin,
(B2) herbicides which are effective selectively in soybeans against dicotyledonous harmful plants, selected from the group consisting of chlortoluron, bentazone, oxyfluorfen, lactofen, fomesafen, flumiclorac, acifluorfen, 2,4-DB, 2,4-D, chlorimuron, diclosulam, fluthiacet, cloransulam and oxasulfuron,
(B3) foliar -and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, haloxyfop-P and propaquizafop or
(B5) nonselective herbicides which can be employed in soybeans for specific purposes, selected from the group consisting of paraquat or
and optionally at least one safener,
whereby the soybean crops are tolerant to the herbicides (A) and (B) which form a constituent of the combination.

64. The method of claim 63, wherein
(B) one or more herbicides is selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, flumetsulam, alachlor and fluthiamide,
(B2) foliar-acting and/or soil-acting herbicides which are effective selectively in soybeans against dicotyledonous harmful plants, selected from the group consisting of oxyfluorfen, lactofen, fomesafen, flumiclorac and cloransulam;
(B3) foliar- and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, and haloxyfop-P;
and optionally at least one safener,
whereby the soybean crops are tolerant to the herbicides (A) and (B) which form a constituent of the combination.

65. The method according to claim 64, wherein the herbicide (A) is glyphosate-isopropylammonium.

66. The method according to claim 65, wherein the herbicide (B) is selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, alachlor and fluthiamide,
(B2) foliar-acting and/or soil-acting herbicides which are effective selectively in soybeans against dicotyledonous harmful plants, selected from the group consisting of fomesafen, flumiclorac and cloransulam;
(B3) foliar- and soil-acting herbicides which are effective selectively in soybeans against monocotyledonous harmful plants, selected from the group consisting of sethoxydim, cycloxydim and clethodim; and
(B4) foliar-acting herbicides which are effective selectively in soybeans against monocotyledonous harmful plants, selected from the group consisting of quizalofop-P, quizalofop, fenoxprop-P, fenoxaprop, fluazifop-P, fluazifop, haloxyfop, and haloxyfop-P.

67. The method according to claim 66, wherein the herbicide (B) is selected from the group consisting of clomazone, fluthiamide, fomensafen and quizalofop-P.

68. A synergistic herbicidal combination, comprising a synergistic effective amount consisting of: one or more herbicides of group (A3) selected from the group consisting of imidazolinones and one or more herbicides of group (B) according to claim 1.

69. The synergistic herbicidal combination of claim 68, wherein the group (A3) herbicide is imazamox.

70. The synergistic herbicidal combination of claim 69, wherein the one or more herbicides of group (B) is selected from the group consisting of clomazone, alachlor, cycloxydim, fluazifop, haloxyfop-P, propaquizafop, metribuzin, pendimethalin, metolachlor, dimethenamid, acifluorfen, chlortoluron, thifensulfuron, oxyfluorfen, lactofen, fomesafen, flumiclorac and cloransulam.

71. A method for regulating the growth of soybean plants, comprising applying a synergistically effective amount of a synergistic herbicidal combination according to claim 68 to said plants.

72. The method according to claim 71, wherein the yield on constituents of soybean plants are influenced.

73. A method of controlling harmful plants in soybean crops, comprising applying post-emergence to the plants, parts of the plants, seeds of the plants or the area under cultivation a synergistic effective amount of a herbicidal combination comprising:

(A) a broad-spectrum herbicide selected from the group consisting of:
(A2) compounds of the formula (A2) and their salts,

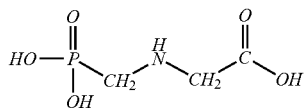

and
(B) one or more herbicides selected from the group consisting of:
(B1) foliar-acting and/or soil-acting herbicides which are effective selectively in soybeans against monocotyledonous and predominantly dicotyledonous harmful plants, selected from the group consisting of trifluralin, clomazone, flumetsulam, alachlor, sulfentrazone, ethalfluralin, fluthiamide, vernolate and flumioxazin,
(B2) herbicides which are effective selectively in soybeans against dicotyledonous harmful plants, selected from the group consisting of chlortoluron, oxyfluorfen, lactofen, fomesafen, flumiclorac, 2,4-DB, 2,4-D, diclosulam and cloransulam,
(B3) foliar- and soil-acting herbicides which are effective selectively in soybeans against monocotyledonous harmful plants, selected from the group consisting of sethoxydim, cycloxydim and clethodim,
(B4) foliar-acting herbicides which are effective selectively in soybeans against monocotyledonous harmful plants, selected from the group consisting of quizalofop-P, quizalofop, fenoxaprop-P, fenoxaprop, fluazifop-P, fluazifop, haloxyfop, haloxyfop-P and propaquizafop or
(B5) nonselective herbicides which can be employed in soybeans for specific purposes, selected from the group consisting of paraquat;
and optionally at least one safener, whereby the soybean crops are tolerant to the herbicides (A) and (B) which form a constituent of the combination,
wherein the ratio of (A) to (B) by weight is from 2000:1 to 1:2000.

74. The method as claimed in claim 73 wherein the ratio of (A) to (B) by weight is from 2000:1 to 1:1000.

75. The method as claimed in claim 73 wherein the ratio of (A) to (B) by weight is from 200:1 to 1:200.

76. The method as claimed in claim 73 wherein (B1) is trifluralin and the ratio of (A2) to (B1) by weight is from 200:1 to 1:50.

77. The method as claimed in claim 73 wherein (B1) is clomazone and the ratio of (A2) to (B1) by weight is from 200:1 to 1:50.

78. The method as claimed in claim 73 wherein (B1) is flumetsulam and the ratio of (A2) to (B1) by weight is from 200:1 to 1:50.

79. The method as claimed in claim 73 wherein (B1) is alachlor and the ratio of (A2) to (B1) by weight is from 200:1 to 1:50.

80. The method as claimed in claim 73 wherein (B1) is sulfentrazone and the ratio of (A2) to (B1) by weight is from 200:1 to 1:50.

81. The method as claimed in claim 73 wherein (B1) is ethalfluralin and the ratio of (A2) to (B1) by weight is from 200:1 to 1:50.

82. The method as claimed in claim 73 wherein (B1) is fluthiamide and the ratio of (A2) to (B1) by weight is from 200:1 to 1:50.

83. The method as claimed in claim 73 wherein (B1) is vernolate and the ratio of (A2) to (B1) by weight is from 200:1 to 1:50.

84. The method as claimed in claim 73 wherein (B1) is flumioxazin and the ratio of (A2) to (B1) by weight is from 200:1 to 1:50.

85. The method as claimed in claim 73 wherein (B2) is chlortoluron and the ratio of (A2) to (B2) by weight is from 300:1 to 1:200.

86. The method as claimed in claim 73 wherein (B2) is oxyfluorfen and the ratio of (A2) to (B2) by weight is from 300:1 to 1:200.

87. The method as claimed in claim 73 wherein (B2) is lactofen and the ratio of (A2) to (B2) by weight is from 300:1 to 1:200.

88. The method as claimed in claim 73 wherein (B2) is fomesafen and the ratio of (A2) to (B2) by weight is from 300:1 to 1:200.

89. The method as claimed in claim 73 wherein (B2) is flumiclorac and the ratio of (A2) to (B2) by weight is from 300:1 to 1:200.

90. The method as claimed in claim 73 wherein (B2) is 2,4-DB and the ratio of (A2) to (B2) by weight is from 300:1 to 1:200.

91. The method as claimed in claim 73 wherein (B2) is 2,4-D and the ratio of (A2) to (B2) by weight is from 300:1 to 1:200.

92. The method as claimed in claim 73 wherein (B2) is diclosulam and the ratio of (A2) to (B2) by weight is from 300:1 to 1:200.

93. The method as claimed in claim 73 wherein (B2) is cloransulam and the ratio of (A2) to (B2) by weight is from 300:1 to 1:200.

94. The method as claimed in claim 73 wherein (B2) is sethoxydim and the ratio of (A2) to (B2) by weight is from 200:1 to 1:100.

95. The method as claimed in claim 73 wherein (B2) is cycloxydim and the ratio of (A2) to (B2) by weight is from 200:1 to 1:100.

96. The method as claimed in claim 73 wherein (B2) is clethodim and the ratio of (A2) to (B2) by weight is from 200:1 to 1:100.

97. The method as claimed in claim 73 wherein (B2) is quizalofop-P and the ratio of (A2) to (B2) by weight is from 100:1 to 1:10.

98. The method as claimed in claim 73 wherein (B2) is quizalofop and the ratio of (A2) to (B2) by weight is from 100:1 to 1:10.

99. The method as claimed in claim 73 wherein (B2) is fenoxaprop-P and the ratio of (A2) to (B2) by weight is from 100:1 to 1:10.

100. The method as claimed in claim 73 wherein (B2) is fenoxaprop and the ratio of (A2) to (B2) by weight is from 100:1 to 1:10.

101. The method as claimed in claim 73 wherein (B2) is fluazifop-P and the ratio of (A2) to (B2) by weight is from 100:1 to 1:10.

* * * * *